US011139603B2

(12) United States Patent
 Conger

(10) Patent No.: US 11,139,603 B2
(45) Date of Patent: Oct. 5, 2021

(54) CONNECTORS WITH SPRING CONTACTS FOR ELECTRICAL STIMULATION SYSTEMS AND METHODS OF MAKING AND USING SAME

(71) Applicant: Boston Scientific Neuromodulation Corporation, Valencia, CA (US)

(72) Inventor: Steven Roger Conger, Agua Dulce, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 418 days.

(21) Appl. No.: 16/149,868

(22) Filed: Oct. 2, 2018

(65) Prior Publication Data

US 2019/0103696 A1  Apr. 4, 2019

Related U.S. Application Data

(60) Provisional application No. 62/567,400, filed on Oct. 3, 2017.

(51) Int. Cl.
 *A61N 1/375* (2006.01)
 *A61N 1/372* (2006.01)
 (Continued)

(52) U.S. Cl.
 CPC .......... *H01R 13/33* (2013.01); *A61N 1/3752* (2013.01); *H01R 13/111* (2013.01); *H01R 13/187* (2013.01); *H01R 13/514* (2013.01); *H01R 13/5202* (2013.01); *H01R 13/5219* (2013.01); *H01R 24/58* (2013.01); *A61N 1/05* (2013.01);
 (Continued)

(58) Field of Classification Search
 CPC ...... A61N 1/0551; A61N 1/3752; A61N 1/05; A61N 1/37235; H01R 13/2421; H01R 2201/12; H01R 24/58; H01R 25/006
 See application file for complete search history.

(56) References Cited

U.S. PATENT DOCUMENTS 3,222,471 A  12/1965  Steinkamp
3,601,747 A  8/1971  Prall et al.
(Continued)

FOREIGN PATENT DOCUMENTS

EP  0580928 A1  2/1994
EP  0650694 B1  7/1998
(Continued)

*Primary Examiner* — Jon Eric C Morales
(74) *Attorney, Agent, or Firm* — Branch Partners PLLC; Bruce E. Black

(57) ABSTRACT

A connector assembly includes a connector body with an elongated shape and a longitudinal axis. The connector body defines a port at a first end configured to receive a proximal portion of a lead or lead extension. Contact assemblies are axially spaced-apart within the connector body and collectively form a lumen that extends from the port along the longitudinal axis of the connector body. Each contact assembly includes a spring contact disposed within a contact housing. The spring contact has a contact region that extends diagonally with respect to the longitudinal axis of the connector body. The contact region is positioned within the contact housing so that insertion of the proximal portion of the lead or lead extension into the contact housing results in a bending deflection of the contact region of the spring contact while maintaining contact between the contact region and the lead or lead extension.

20 Claims, 18 Drawing Sheets

(51) Int. Cl.
*A61N 1/05* (2006.01)
*H01R 13/33* (2006.01)
*H01R 13/11* (2006.01)
*H01R 13/52* (2006.01)
*H01R 13/514* (2006.01)
*H01R 13/187* (2006.01)
*H01R 24/58* (2011.01)

(52) U.S. Cl.
CPC ...... *H01R 13/5224* (2013.01); *H01R 2201/12* (2013.01)

(56) References Cited

U.S. PATENT DOCUMENTS

| | | | |
|---|---|---|---|
| 3,718,142 | A | 2/1973 | Mulier |
| 3,757,789 | A | 9/1973 | Shanker |
| 3,771,106 | A | 11/1973 | Matsumoto et al. |
| 3,908,668 | A | 9/1975 | Bolduc |
| 3,951,154 | A | 4/1976 | Hartlaub |
| 3,990,727 | A | 11/1976 | Gallagher |
| 4,003,616 | A | 1/1977 | Springer |
| 4,112,953 | A | 9/1978 | Shanker et al. |
| 4,142,532 | A | 3/1979 | Ware |
| 4,180,078 | A | 12/1979 | Anderson |
| 4,245,642 | A | 1/1981 | Skubitz et al. |
| 4,259,962 | A | 4/1981 | Peers-Trevarton |
| 4,310,001 | A | 1/1982 | Comben |
| 4,364,625 | A | 12/1982 | Baker et al. |
| 4,367,907 | A | 1/1983 | Buck |
| 4,411,276 | A | 10/1983 | Dickhudt et al. |
| 4,411,277 | A | 10/1983 | Dickhudt |
| 4,461,194 | A | 7/1984 | Moore |
| 4,466,441 | A | 8/1984 | Skubitz et al. |
| 4,516,820 | A | 5/1985 | Kuzma |
| RE31,990 | E | 9/1985 | Sluetz et al. |
| 4,540,236 | A | 9/1985 | Peers-Trevarton |
| 4,602,624 | A | 7/1986 | Naples et al. |
| 4,603,696 | A | 8/1986 | Cross, Jr. et al. |
| 4,614,395 | A | 9/1986 | Peers-Trevarton |
| 4,630,611 | A | 12/1986 | King |
| 4,695,116 | A | 9/1987 | Bailey et al. |
| 4,695,117 | A | 9/1987 | Kysiak |
| 4,712,557 | A | 12/1987 | Harris |
| 4,715,380 | A | 12/1987 | Harris |
| 4,744,370 | A | 5/1988 | Harris |
| 4,784,141 | A | 11/1988 | Peers-Trevarton |
| 4,832,032 | A | 5/1989 | Schneider |
| 4,840,580 | A | 6/1989 | Saell et al. |
| 4,850,359 | A | 7/1989 | Putz |
| 4,860,750 | A | 8/1989 | Frey et al. |
| 4,867,708 | A | 9/1989 | Iizuka |
| 4,869,255 | A | 9/1989 | Putz |
| 4,898,173 | A | 2/1990 | Daglow et al. |
| 4,899,753 | A | 2/1990 | Inoue et al. |
| 4,951,687 | A | 8/1990 | Ufford et al. |
| 4,995,389 | A | 2/1991 | Harris |
| 5,000,177 | A | 3/1991 | Hoffman et al. |
| 5,000,194 | A | 3/1991 | van den Honert et al. |
| 5,007,435 | A | 4/1991 | Doan et al. |
| 5,007,864 | A | 4/1991 | Stutz, Jr. |
| 5,070,605 | A | 12/1991 | Daglow et al. |
| 5,082,453 | A | 1/1992 | Stutz, Jr. |
| 5,086,773 | A | 2/1992 | Ware |
| 5,135,001 | A | 8/1992 | Sinofsky et al. |
| 5,193,539 | A | 3/1993 | Schulman et al. |
| 5,193,540 | A | 3/1993 | Schulman et al. |
| 5,201,865 | A | 4/1993 | Kuehn |
| 5,241,957 | A | 9/1993 | Camps et al. |
| 5,252,090 | A | 10/1993 | Giurtino et al. |
| 5,261,395 | A | 11/1993 | Oleen et al. |
| 5,312,439 | A | 5/1994 | Loeb |
| 5,324,312 | A | 6/1994 | Stokes et al. |
| 5,330,521 | A | 7/1994 | Cohen |
| 5,336,246 | A | 8/1994 | Dantanarayana |
| 5,348,481 | A | 9/1994 | Ortiz |
| 5,354,326 | A | 10/1994 | Comben et al. |
| 5,358,514 | A | 10/1994 | Schulman et al. |
| 5,368,496 | A | 11/1994 | Ranalletta et al. |
| 5,374,279 | A | 12/1994 | Duffin, Jr. et al. |
| 5,374,285 | A | 12/1994 | Vaiani et al. |
| 5,383,913 | A | 1/1995 | Schiff |
| 5,413,595 | A | 5/1995 | Stutz, Jr. |
| 5,433,734 | A | 7/1995 | Stokes et al. |
| 5,435,731 | A | 7/1995 | Kang |
| 5,458,629 | A | 10/1995 | Baudino et al. |
| 5,486,202 | A | 1/1996 | Bradshaw |
| 5,489,225 | A | 2/1996 | Julian |
| 5,509,928 | A | 4/1996 | Acken |
| 5,522,874 | A | 6/1996 | Gates |
| 5,534,019 | A | 7/1996 | Paspa |
| 5,545,188 | A | 8/1996 | Bradshaw et al. |
| 5,545,189 | A | 8/1996 | Fayram |
| 5,582,180 | A | 8/1996 | Manset et al. |
| 5,560,358 | A | 10/1996 | Arnold et al. |
| 5,679,026 | A | 10/1997 | Fain et al. |
| 5,683,433 | A | 11/1997 | Carson |
| 5,711,316 | A | 1/1998 | Elsberry et al. |
| 5,713,922 | A | 2/1998 | King |
| 5,720,631 | A | 2/1998 | Carson et al. |
| 5,730,628 | A | 3/1998 | Hawkins |
| 5,755,743 | A | 5/1998 | Volz et al. |
| 5,766,042 | A | 6/1998 | Ries et al. |
| 5,782,892 | A | 7/1998 | Castle et al. |
| 5,796,044 | A | 8/1998 | Cobian et al. |
| 5,800,350 | A | 9/1998 | Coppleson et al. |
| 5,800,495 | A | 9/1998 | Machek et al. |
| 5,807,144 | A | 9/1998 | Sivard |
| 5,837,006 | A | 11/1998 | Ocel et al. |
| 5,843,141 | A | 12/1998 | Bischoff et al. |
| 5,843,148 | A | 12/1998 | Gijsbers et al. |
| 5,906,634 | A | 5/1999 | Flynn et al. |
| 5,931,861 | A | 8/1999 | Werner et al. |
| 5,938,688 | A | 8/1999 | Schiff |
| 5,951,595 | A | 9/1999 | Moberg et al. |
| 5,968,082 | A | 10/1999 | Heil |
| 5,987,361 | A | 11/1999 | Mortimer |
| 5,989,077 | A | 11/1999 | Mast et al. |
| 6,006,135 | A | 12/1999 | Kast et al. |
| 6,018,684 | A | 1/2000 | Bartig et al. |
| 6,038,479 | A | 3/2000 | Werner et al. |
| 6,038,481 | A | 3/2000 | Werner et al. |
| 6,042,432 | A | 3/2000 | Hashizawa et al. |
| 6,051,017 | A | 4/2000 | Loeb et al. |
| 6,080,188 | A | 6/2000 | Rowley et al. |
| 6,112,120 | A | 8/2000 | Correas |
| 6,112,121 | A | 8/2000 | Paul et al. |
| 6,125,302 | A | 9/2000 | Kuzma |
| 6,134,478 | A | 10/2000 | Spehr |
| 6,154,678 | A | 11/2000 | Lauro |
| 6,161,047 | A | 12/2000 | King et al. |
| 6,162,101 | A | 12/2000 | Fischer et al. |
| 6,164,284 | A | 12/2000 | Schulman et al. |
| 6,167,311 | A | 12/2000 | Rezai |
| 6,167,314 | A | 12/2000 | Fischer, Sr. et al. |
| 6,175,710 | B1 | 1/2001 | Kamaji et al. |
| 6,181,969 | B1 | 1/2001 | Gord |
| 6,185,452 | B1 | 2/2001 | Schulman et al. |
| 6,192,278 | B1 | 2/2001 | Werner et al. |
| 6,198,969 | B1 | 3/2001 | Kuzma |
| 6,208,894 | B1 | 3/2001 | Schulman et al. |
| 6,224,450 | B1 | 5/2001 | Norton |
| 6,271,094 | B1 | 8/2001 | Boyd et al. |
| 6,295,944 | B1 | 10/2001 | Lovett |
| 6,319,021 | B1 | 11/2001 | Billman |
| 6,321,126 | B1 | 11/2001 | Kuzma |
| 6,322,559 | B1 | 11/2001 | Daulton et al. |
| 6,343,233 | B1 | 1/2002 | Werner et al. |
| 6,364,278 | B1 | 4/2002 | Lin et al. |
| 6,370,434 | B1 | 4/2002 | Zhang et al. |
| 6,391,985 | B1 | 5/2002 | Goode et al. |
| 6,397,108 | B1 | 5/2002 | Camps et al. |
| 6,415,168 | B1 | 7/2002 | Putz |
| 6,428,336 | B1 | 8/2002 | Akerfeldt |
| 6,428,368 | B1 | 8/2002 | Hawkins et al. |

(56) References Cited

U.S. PATENT DOCUMENTS

| | | |
|---|---|---|
| 6,430,442 B1 | 8/2002 | Peters et al. |
| 6,466,824 B1 | 10/2002 | Struble |
| 6,473,654 B1 | 10/2002 | Chinn |
| 6,498,952 B2 | 12/2002 | Imani et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,604,283 B1 | 8/2003 | Kuzma |
| 6,605,094 B1 | 8/2003 | Mann et al. |
| 6,609,029 B1 | 8/2003 | Mann et al. |
| 6,609,032 B1 | 8/2003 | Woods et al. |
| 6,654,641 B1 | 11/2003 | Froberg |
| 6,662,035 B2 | 12/2003 | Sochor |
| 6,663,570 B2 | 12/2003 | Mott |
| 6,671,534 B2 | 12/2003 | Putz |
| 6,671,553 B1 | 12/2003 | Helland et al. |
| 6,678,564 B2 | 1/2004 | Ketterl et al. |
| 6,741,892 B1 | 5/2004 | Meadows et al. |
| 6,752,096 B2 | 6/2004 | Elson et al. |
| 6,757,039 B2 | 6/2004 | Ma |
| 6,757,970 B1 | 7/2004 | Kuzma et al. |
| 6,799,991 B2 | 10/2004 | Williams et al. |
| 6,805,675 B1 | 10/2004 | Gardeski et al. |
| 6,854,994 B2 | 2/2005 | Stein et al. |
| 6,878,013 B1 | 4/2005 | Behan |
| 6,895,276 B2 | 5/2005 | Kast et al. |
| 6,895,280 B2 | 5/2005 | Meadows et al. |
| 6,913,478 B2 | 7/2005 | Lamirey |
| 6,921,295 B2 | 7/2005 | Sommer et al. |
| 6,968,235 B2 | 11/2005 | Belden et al. |
| 6,980,863 B2 | 12/2005 | van Venrooij et al. |
| 7,027,852 B2 | 4/2006 | Helland |
| 7,047,084 B2 | 5/2006 | Erickson et al. |
| 7,058,452 B2 | 6/2006 | Dahlberg |
| 7,069,081 B2 | 6/2006 | Biggs et al. |
| 7,083,474 B1 | 8/2006 | Fleck et al. |
| 7,108,549 B2 | 9/2006 | Lyu et al. |
| 7,110,827 B2 | 9/2006 | Sage et al. |
| 7,128,600 B2 | 10/2006 | Osypka |
| 7,155,283 B2 | 12/2006 | Ries et al. |
| 7,164,951 B2 | 1/2007 | Ries et al. |
| 7,168,165 B2 | 1/2007 | Calzada et al. |
| 7,191,009 B2 | 3/2007 | Laske et al. |
| 7,195,523 B2 | 3/2007 | Naviaux |
| 7,203,548 B2 | 4/2007 | Whitehurst et al. |
| 7,225,034 B2 | 5/2007 | Ries et al. |
| 7,231,253 B2 | 6/2007 | Tidemand et al. |
| 7,241,180 B1 | 7/2007 | Rentas |
| 7,242,987 B2 | 7/2007 | Holleman et al. |
| 7,244,150 B1 | 7/2007 | Brase et al. |
| 7,270,568 B2 | 9/2007 | Osypka |
| 7,283,878 B2 | 10/2007 | Brostrom et al. |
| 7,286,882 B2 | 10/2007 | Cole |
| 7,287,995 B2 | 10/2007 | Stein et al. |
| 7,292,890 B2 | 11/2007 | Whitehurst et al. |
| 7,396,335 B2 | 7/2008 | Gardeski et al. |
| 7,402,083 B2 | 7/2008 | Kast et al. |
| 7,422,487 B2 | 9/2008 | Osypka |
| 7,430,958 B2 | 10/2008 | Wong |
| 7,437,193 B2 | 10/2008 | Parramon et al. |
| 7,450,997 B1 | 11/2008 | Pianca et al. |
| 7,489,971 B1 | 2/2009 | Franz |
| 7,512,446 B2 | 3/2009 | Honeck |
| 7,516,447 B2 | 3/2009 | Drew |
| 7,526,339 B2 | 4/2009 | Lahti et al. |
| 7,539,542 B1 | 5/2009 | Malinowski |
| 7,548,788 B2 | 6/2009 | Chinn et al. |
| 7,554,493 B1 | 6/2009 | Rahman |
| 7,583,999 B2 | 9/2009 | Bedenbaugh |
| 7,585,190 B2 | 9/2009 | Osypka |
| 7,650,184 B2 | 1/2010 | Walter |
| 7,668,601 B2 | 2/2010 | Hegland et al. |
| 7,672,734 B2 | 3/2010 | Anderson et al. |
| 7,736,191 B1 | 6/2010 | Sochor |
| 7,758,384 B2 | 7/2010 | Alexander et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,809,446 B2 | 10/2010 | Meadows |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,046,074 B2 | 10/2011 | Barker |
| 8,078,280 B2 | 12/2011 | Sage |
| 8,099,177 B2 | 1/2012 | Dahlberg |
| 8,100,726 B2 | 1/2012 | Harlan et al. |
| 8,140,163 B1 | 3/2012 | Daglow et al. |
| 8,167,660 B2 | 5/2012 | Dilmaghanian et al. |
| 8,175,710 B2 | 5/2012 | He |
| 8,190,259 B1 | 5/2012 | Smith et al. |
| 8,206,180 B1 | 6/2012 | Kast et al. |
| 8,224,450 B2 | 7/2012 | Brase |
| 8,225,504 B2 | 7/2012 | Dye et al. |
| 8,239,042 B2 | 8/2012 | Chinn et al. |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,412,330 B2 | 4/2013 | Kast et al. |
| 8,527,054 B2 | 9/2013 | North |
| 8,583,237 B2 | 11/2013 | Bedenbaugh |
| 8,600,507 B2 | 12/2013 | Brase et al. |
| 8,682,439 B2 | 3/2014 | DeRohan et al. |
| 8,688,235 B1 | 4/2014 | Pianca et al. |
| 8,694,103 B2 | 4/2014 | Barker |
| 8,761,887 B2 | 6/2014 | Schramm et al. |
| 8,784,143 B2 | 7/2014 | Edgell et al. |
| 8,831,742 B2 | 9/2014 | Pianca et al. |
| 8,849,396 B2 | 9/2014 | DeRohan et al. |
| 8,849,415 B2 | 9/2014 | Bedenbaugh |
| 8,897,876 B2 | 11/2014 | Sundaramurthy et al. |
| 8,897,891 B2 | 11/2014 | Romero |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,270,070 B2 | 2/2016 | Pianca |
| 9,289,596 B2 | 3/2016 | Leven |
| 9,352,147 B2 | 5/2016 | Nguyen-stella et al. |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,498,618 B2 | 11/2016 | Stetson et al. |
| 9,498,620 B2 | 11/2016 | Romero et al. |
| 9,504,839 B2 | 11/2016 | Leven |
| 9,656,093 B2 | 5/2017 | Villarta et al. |
| 2001/0023368 A1 | 9/2001 | Black et al. |
| 2002/0143376 A1 | 10/2002 | Chinn et al. |
| 2002/0156513 A1 | 10/2002 | Borkan |
| 2002/0183817 A1 | 12/2002 | Van Venrooij et al. |
| 2003/0163171 A1 | 8/2003 | Kast et al. |
| 2004/0064164 A1 | 4/2004 | Ries et al. |
| 2004/0230268 A1 | 11/2004 | Huff et al. |
| 2004/0260373 A1 | 12/2004 | Ries et al. |
| 2005/0015130 A1 | 1/2005 | Gill |

(56) References Cited

U.S. PATENT DOCUMENTS

| | | |
|---|---|---|
| 2005/0027326 A1 | 2/2005 | Ries et al. |
| 2005/0027327 A1 | 2/2005 | Ries et al. |
| 2005/0038489 A1 | 2/2005 | Grill |
| 2005/0043770 A1 | 2/2005 | Hine et al. |
| 2005/0043771 A1 | 2/2005 | Sommer et al. |
| 2005/0137665 A1 | 6/2005 | Cole |
| 2005/0171587 A1 | 8/2005 | Daglow et al. |
| 2005/0186829 A1 | 8/2005 | Balsells |
| 2005/0272280 A1 | 12/2005 | Osypka |
| 2006/0004419 A1 | 1/2006 | Olbertz |
| 2006/0015163 A1 | 1/2006 | Brown |
| 2006/0025841 A1 | 2/2006 | McIntyre |
| 2006/0030918 A1 | 2/2006 | Chinn |
| 2006/0167522 A1 | 7/2006 | Malinowski |
| 2006/0224208 A1 | 10/2006 | Naviaux |
| 2006/0247697 A1 | 11/2006 | Sharma et al. |
| 2006/0247749 A1 | 11/2006 | Colvin |
| 2006/0259106 A1 | 11/2006 | Arnholdt et al. |
| 2007/0042648 A1 | 2/2007 | Balsells |
| 2007/0142889 A1 | 6/2007 | Whitehurst et al. |
| 2007/0150036 A1 | 6/2007 | Anderson |
| 2007/0161294 A1 | 7/2007 | Brase et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0139031 A1 | 6/2008 | Ries et al. |
| 2008/0177167 A1 | 7/2008 | Janzig et al. |
| 2008/0208277 A1 | 8/2008 | Janzig et al. |
| 2008/0208278 A1 | 8/2008 | Janzig et al. |
| 2008/0208279 A1 | 8/2008 | Janzig et al. |
| 2008/0215125 A1 | 9/2008 | Farah et al. |
| 2008/0255647 A1 | 10/2008 | Jensen et al. |
| 2008/0274651 A1 | 11/2008 | Boyd et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0264943 A1 | 10/2009 | Barker |
| 2009/0276021 A1 | 11/2009 | Meadows et al. |
| 2009/0287191 A1 | 11/2009 | Ferren et al. |
| 2010/0029127 A1 | 2/2010 | Sjostedt |
| 2010/0030298 A1 | 2/2010 | Martens et al. |
| 2010/0036468 A1 | 2/2010 | Decre et al. |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0022100 A1 | 1/2011 | Brase et al. |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0184480 A1 | 7/2011 | Kast et al. |
| 2011/0238129 A1 | 9/2011 | Moffitt et al. |
| 2011/0245903 A1 | 10/2011 | Schulte et al. |
| 2011/0270330 A1 | 11/2011 | Janzig et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0053646 A1 | 3/2012 | Brase et al. |
| 2012/0071937 A1 | 3/2012 | Sundaramurthy et al. |
| 2012/0071949 A1 | 3/2012 | Pianca et al. |
| 2012/0165911 A1 | 6/2012 | Pianca |
| 2012/0185019 A1 | 7/2012 | Schramm et al. |
| 2012/0197375 A1 | 8/2012 | Pianca et al. |
| 2012/0203302 A1 | 8/2012 | Moffit et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0253443 A1 | 10/2012 | Dilmaghanian et al. |
| 2012/0259386 A1 | 10/2012 | DeRohan et al. |
| 2012/0316615 A1 | 12/2012 | DiGiore et al. |
| 2013/0053864 A1 | 2/2013 | Geroy et al. |
| 2013/0098678 A1 | 4/2013 | Barker |
| 2013/0105071 A1 | 5/2013 | DiGiore et al. |
| 2013/0109254 A1 | 5/2013 | Klardie et al. |
| 2013/0110205 A1 | 5/2013 | Lim et al. |
| 2013/0116754 A1 | 5/2013 | Sharma et al. |
| 2013/0149031 A1 | 6/2013 | Changsrivong et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0218154 A1 | 8/2013 | Carbunaru |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0148885 A1 | 5/2014 | DeRohan et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0025609 A1 | 1/2015 | Govea |
| 2015/0045864 A1 | 2/2015 | Howard |
| 2015/0066120 A1 | 3/2015 | Govea |
| 2015/0151113 A1 | 6/2015 | Govea et al. |
| 2015/0209575 A1 | 7/2015 | Black |
| 2015/0360023 A1 | 12/2015 | Howard et al. |
| 2015/0374978 A1 | 12/2015 | Howard et al. |
| 2015/0375002 A1 | 12/2015 | Janzig et al. |
| 2016/0059019 A1 | 3/2016 | Malinowski et al. |
| 2016/0129242 A1 | 5/2016 | Malinowski |
| 2016/0129265 A1 | 5/2016 | Malinowski |
| 2016/0158558 A1 | 6/2016 | Shanahan et al. |
| 2016/0206891 A1 | 7/2016 | Howard et al. |
| 2016/0228692 A1 | 8/2016 | Steinke et al. |
| 2016/0296745 A1 | 10/2016 | Govea et al. |
| 2017/0014635 A1 | 1/2017 | Villarta et al. |
| 2017/0025779 A1 | 1/2017 | Dilmaghanian et al. |
| 2017/0072187 A1 | 3/2017 | Howard et al. |
| 2017/0143978 A1 | 5/2017 | Barker |
| 2017/0203104 A1 | 7/2017 | Nageri et al. |
| 2017/0361108 A1 | 12/2017 | Leven |
| 2018/0008832 A1 | 1/2018 | Leven |
| 2018/0028820 A1 | 2/2018 | Nageri |
| 2018/0093098 A1 | 4/2018 | Nageri et al. |
| 2018/0369596 A1 | 12/2018 | Funderburk |

FOREIGN PATENT DOCUMENTS

| | | |
|---|---|---|
| EP | 0832667 B1 | 2/2004 |
| EP | 1181947 B1 | 1/2006 |
| EP | 1625875 | 2/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |

(56) References Cited

FOREIGN PATENT DOCUMENTS

| | | |
|---|---|---|
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

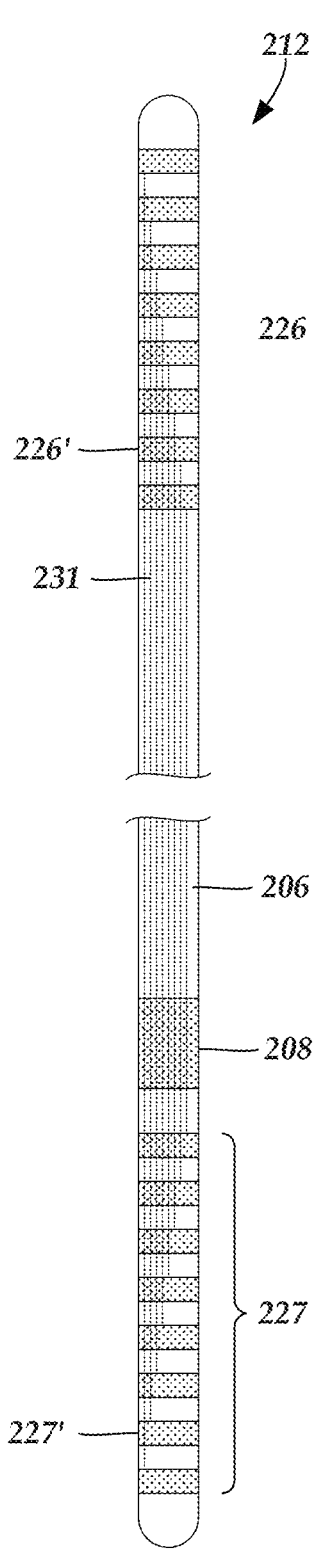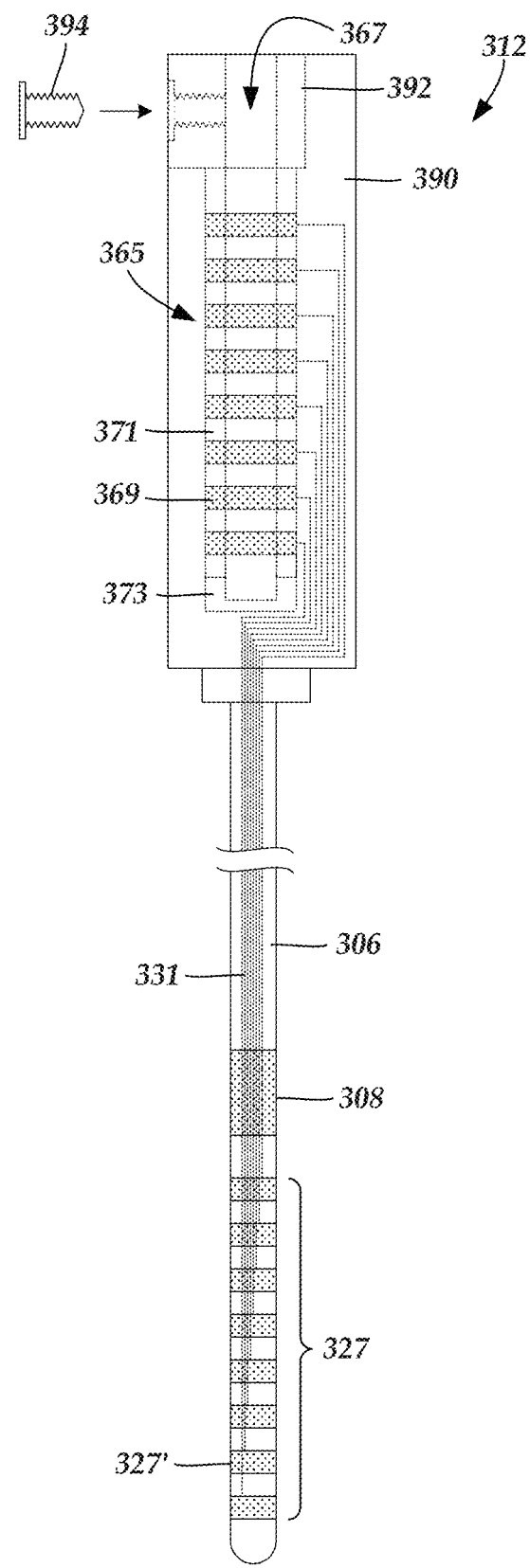
Fig. 2
Fig. 3

CONNECTORS WITH SPRING CONTACTS FOR ELECTRICAL STIMULATION SYSTEMS AND METHODS OF MAKING AND USING SAME

CROSS-REFERENCE TO RELATED APPLICATIONS

This application claims the benefit under 35 U.S.C. § 119(e) of U.S. Provisional Patent Application Ser. No. 62/567,400, filed Oct. 3, 2017, which is incorporated herein by reference.

FIELD

The present invention is directed to the area of implantable electrical stimulation systems and methods of making and using the systems. The present invention is also directed to implantable electrical stimulation systems having connectors with spring type contacts and contact assemblies, as well as methods of making and using the contacts, contact assemblies, connectors, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a connector assembly includes a connector body having an elongated shape with a first end, an opposing second end, and a longitudinal axis. The connector body defines a port at the first end configured to receive a proximal portion of a lead or lead extension. Contact assemblies are axially spaced-apart within the connector body and collectively form a lumen that extends from the port along the longitudinal axis of the connector body. Each contact assembly includes a spring contact disposed within a contact housing. The spring contact has a contact region that extends diagonally with respect to the longitudinal axis of the connector body. The contact region is positioned within the contact housing so that insertion of the proximal portion of the lead or lead extension into the contact housing results in a bending deflection of the contact region of the spring contact while maintaining contact between the contact region and the lead or lead extension.

In at least some embodiments, the contact housing includes a first sidewall, an opposing second sidewall, an outer circumferential surface extending between the first and second sidewalls, and an inner circumferential surface also extending between, and inset from, the first and second sidewalls and forming a portion of the lumen. The inner circumferential surface defines a pocket bound by the first sidewall and the second sidewall. The spring contact is disposed in the pocket and further includes a first bend, a second bend, with the contact region extending between the first bend and the second bend. The spring contact urges the first bend to press against the first sidewall and the second bend to press against the interior surface of the second sidewall.

In at least some embodiments, the contact region is configured to flex radially outward into the pocket when physically contacting a lead or lead extension received by the port and inserted into the lumen. In at least some embodiments, at least one of the first bend or the second bend is configured to slide circumferentially along the pocket when the contact region flexes radially outward. In at least some embodiments, at least one of the first bend or the bend is attached to the pocket. In at least some embodiments, the spring contact includes at least two first bends and at least two second bends. In at least some embodiments, the spring contact has a first end and an opposing second end, where the first end is urged to press against the interior surface of the first sidewall, and where the second end is urged to press against the interior surface of the second sidewall.

In at least some embodiments, the spring contact is formed as a continuous loop of material. In at least some embodiments, the contact assemblies include a first contact assembly and a second contact assembly, and further including a seal disposed between the first contact assembly and the second contact assembly.

In another embodiment, a lead assembly includes a lead or a lead extension having a proximal portion and a distal portion. The proximal portion of the lead or the lead extension includes terminals electrically insulated from one another. The lead assembly also includes the connector assembly described above.

In yet another embodiment, an electrical stimulating system includes the lead assembly described above and a control module coupled to the lead assembly. The control module includes a housing and an electronic subassembly disposed in the housing. In at least some embodiments, the connector assembly of the lead assembly is part of the control module. In at least some embodiments, the lead assembly includes the lead and the electrical stimulation system further includes a lead extension coupleable to the control module and the lead, where the connector assembly is part of the lead extension.

In still yet another embodiment, a contact assembly includes a contact housing defining a lumen through the contact housing and a longitudinal axis along the lumen, where the contact housing is configured to receive a proximal portion of a lead or lead extension within the lumen of the contact housing. A spring contact is disposed within the contact housing and has a contact region that extends diagonally with respect to longitudinal axis of the contact housing. The contact region is positioned within the contact housing so that insertion of the portion of the lead or lead extension into the contact housing results in a bending deflection of the contact region while maintaining contact between the contact region and the lead or lead extension.

In another embodiment, a connector assembly includes multiple contact assemblies described above arranged in a transverse array with the lumens of the contact housings of the contact assemblies being spaced apart and parallel to each other.

In yet another embodiment, a connector assembly includes multiple contact assemblies described above arranged in an axial array with the lumens of the contact housings of the contact assemblies being aligned to form a connector lumen.

In still yet another embodiment, a connector assembly includes a connector body having an elongated shape with a first end, an opposing second end, an inner circumferential wall, and a longitudinal axis. The connector body defines a port at the first end configured to receive a proximal portion of a lead or lead extension. The port opens to a cavity defined within the connector body and bound, in part, by the inner circumferential wall. A first contact assembly and a second contact assembly are axially spaced-apart from one another within the cavity of the connector body and collectively form a lumen that extends from the port along the longitudinal axis of the connector body. The first and second contact assemblies each include a contact housing having a first sidewall, an opposing second sidewall, and an outer circumferential surface. The contact housing defines circumferential chamfers extending between the outer circumferential surface and each of the first and second sidewalls. A connector contact is disposed in the contact housing and is exposed to the lumen. A seal is disposed within the cavity between the first contact assembly and the second contact assembly. The seal includes a deformable, washer-shaped seal body having an outer circumference and a deformable flange disposed around the outer circumference of the seal body. The seal is positioned between the contact housings of the first and second contact assemblies with the flange positioned between opposing ones of the circumferential chamfers of the first and second contact assemblies.

In at least some embodiments, the deformable seal body is axially compressed between the first and second connector assemblies, the axial compression causing the seal body to expand radially and the deformable flange to form a seal against the inner circumferential wall of the connector body and opposing ones of the circumferential chamfers of the first and second contact assemblies.

In another embodiment, a method for stimulating patient tissue includes advancing a lead to a target stimulation location within a patient. The lead includes electrodes disposed along a distal portion of the lead, terminals disposed along a proximal portion of the lead, and conductors electrically coupling the terminals to the electrodes. The proximal portion of the lead is coupled to the connector assembly described above. Patient tissue is stimulated using the electrodes. In at least some embodiments, coupling the lead to the connector assembly includes physically contacting at least one of the terminals to the contact region of the spring contact of at least one of the contact assemblies. The physical contact causes a bending deflection of the contact region of the spring contact while maintaining contact between the contact region and the lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2 is a schematic side view of one embodiment of an electrical stimulation lead, according to the invention;

FIG. 3 is a schematic side view of one embodiment of a lead extension suitable for coupling with the electrical stimulation lead of FIG. 2, according to the invention;

DETAILED DESCRIPTION

The present invention is directed to the area of implantable electrical stimulation systems and methods of making and using the systems. The present invention is also directed to implantable electrical stimulation systems having connectors with spring type contacts and contact assemblies, as well as methods of making and using the contacts, contact assemblies, connectors, and electrical stimulation systems.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, peripheral nerve, or cardiac-tissue stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglion stimulation, sacral nerve stimulation, or stimulation of other nerves, muscles, and tissues.

Figure 1:
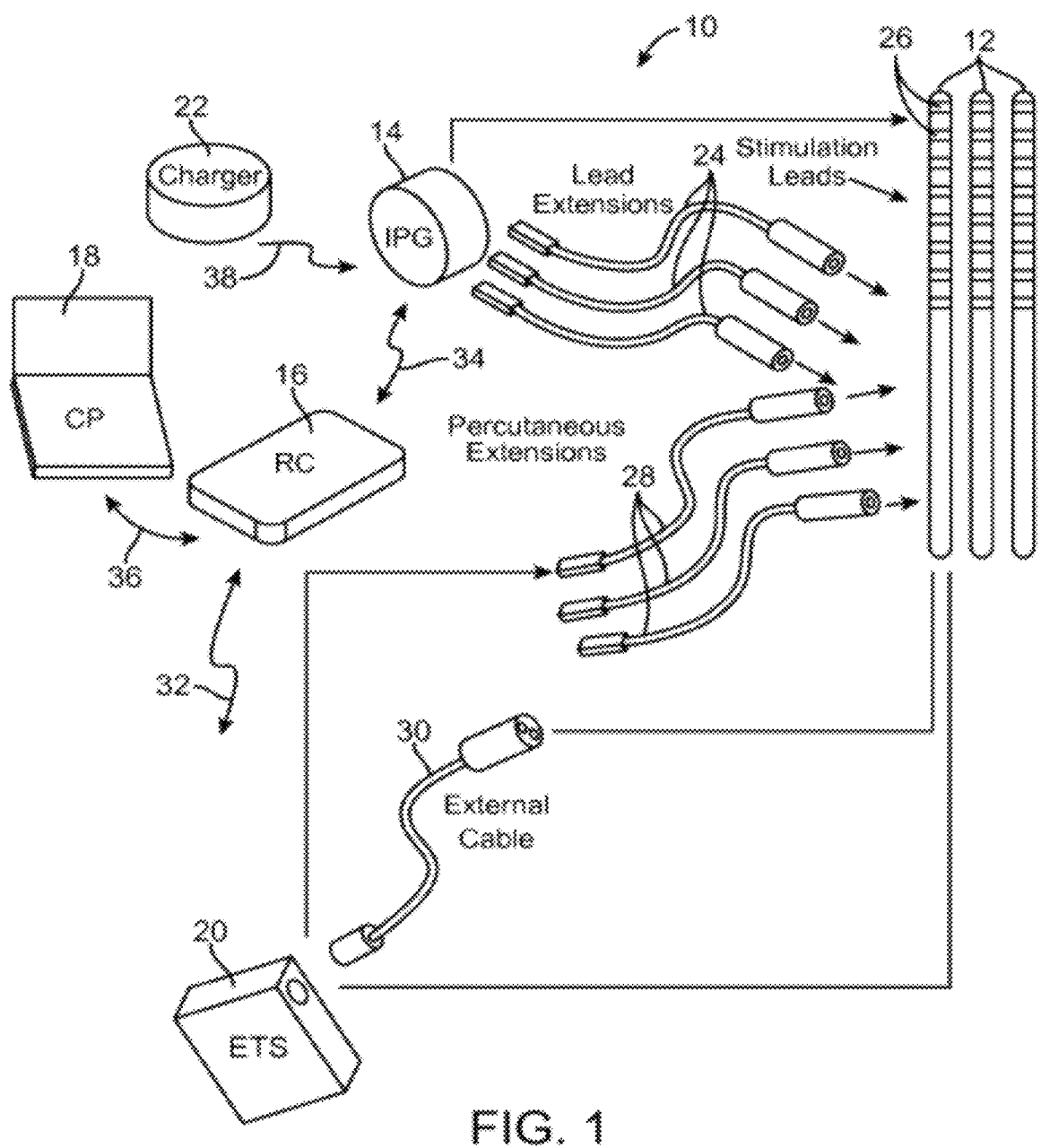
FIG. 1 is a schematic view of one embodiment of an electrical stimulation system, according to the invention.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally, via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Turning to FIG. 2, one or more leads are configured for coupling with a control module. The term "control module" is used herein to describe a pulse generator (e.g., the IPG 14 or the ETS 20 of FIG. 1). Stimulation signals generated by the control module are emitted by electrodes of the lead(s) to stimulate patient tissue. The electrodes of the lead(s) are electrically coupled to terminals of the lead(s) that, in turn, are electrically coupleable with the control module. In some embodiments, the lead(s) couple(s) directly with the control module. In other embodiments, one or more intermediary devices (e.g., a lead extension, an adaptor, a splitter, or the like) are disposed between the lead(s) and the control module.

Percutaneous leads are described herein for clarity of illustration. It will be understood that paddle leads and cuff leads can be used in lieu of, or in addition to, percutaneous leads. The leads described herein include 8 electrodes. It will be understood that the leads could include any suitable number of electrodes. The leads described herein exclusively include ring electrodes. It will be understood that the leads can include a distal-tip electrode, or one or more segmented electrodes in lieu of, or in addition to one or more ring electrodes. Additionally, the term "elongated member" used herein includes leads (e.g., percutaneous, paddle, cuff, or the like), as well as intermediary devices (e.g., lead extensions, adaptors, splitters, or the like).

FIG. 2 shows, in schematic side view, one embodiment of a lead 212 suitable for implanting into a patient and providing electrical stimulation. In some embodiments, the lead 212 is coupled directly to a control module. In other embodiments, the lead 212 is coupled to the control module via one or more intermediary devices. In the illustrated embodiment, an array of electrodes 226, which includes electrode 226', is disposed along a distal portion of a lead body 206 lead and an array of lead terminals 227, which includes lead terminal 227', is disposed along a proximal portion of the lead body. Lead conductors, such as lead conductor 231, extend along a longitudinal length of the lead and electrically couple the array of electrodes 226 to the array lead terminals 227.

Conductors can extend along the longitudinal length of the lead within one or more lumens defined in the lead. In other instances, the conductors may extend along the lead within the lead body itself. The lead 212 includes an retention sleeve 208 disposed along the proximal portion of the body to facilitate coupling of the proximal portion of the lead to a connector. The connector may be disposed along a control module. Alternatively, the retention sleeve 208 can be used to facilitate coupling of the proximal portion of the lead to a connector of an intermediary device, such as a lead extension which, in turn, is coupled to a connector of a control module.

FIG. 3 shows, in schematic side view, one embodiment of a lead extension 312 suitable for implanting into a patient and coupling a lead, such as the lead 212, to a control module. The lead extension 312 includes a lead-extension body 306 having a distal portion and a proximal portion. A lead-extension connector 390 is disposed along the distal portion of the lead-extension body 306 and an array of lead-extension terminals 327, such as lead-extension terminal 327', are disposed along the proximal portion of the lead-extension body 306.

The lead-extension connector 390 contains a lead-extension connector stack 365 that defines a connector lumen 367 configured to receive the proximal portion of an elongated member (e.g., lead 212). The lead-extension connector stack 365 includes lead-extension connector contacts, such as lead-extension connector contact 369, arranged along the connector lumen 367 and configured to electrically couple with terminals of the elongated member (e.g., lead 212) when the proximal portion of the elongated member is received by the lead-extension connector 390. The connector contacts are electrically isolated from one another by electrically-nonconductive spacers, such as spacer 371. In at least some embodiments, the spacers provide at least a partial seal to reduce, or even eliminate, seepage of fluid into the connector from the environment external to the connector. The connector stack may also include an end stop 373 to promote alignment of the elongated-member terminals with the lead-extension connector contacts.

The lead-extension connector 390 further includes a retention assembly for facilitating retention of the proximal portion of the elongated member (e.g., lead 212) when the proximal portion of the elongated member is received by the lead-extension connector 390. In the illustrated embodiment, the retention assembly includes a lead-extension retention block 392. The lead-extension retention block 392 is positioned to align with the retention sleeve (208 in FIG. 2) of the elongated member when the elongated member is received by the lead-extension connector 390. In the illustrated embodiment, the retention assembly further includes a retaining member (e.g., a set screw, a pin, or the like) 394 for pressing the retention sleeve of the inserted elongated member against the retention block to retain inserted elongated member within the lead-extension connector 390.

Lead-extension conductors, such as lead-extension conductor 331, extend along a longitudinal length of the lead extension and electrically couple the lead-extension connector contacts to the array of lead-extension terminals 327. The lead-extension conductors can extend along the longitudinal length of the lead-extension body within one or more lumens defined in the lead extension. In other instances, the lead-extension conductors may extend along the lead extension within the lead-extension body itself. The lead extension 312 includes a retention sleeve 308 disposed along the proximal portion of the lead-extension body to facilitate coupling of the proximal portion of the lead extension to a connector, such as a control-module connector, another lead-extension connector, or the like.

Figure 4:
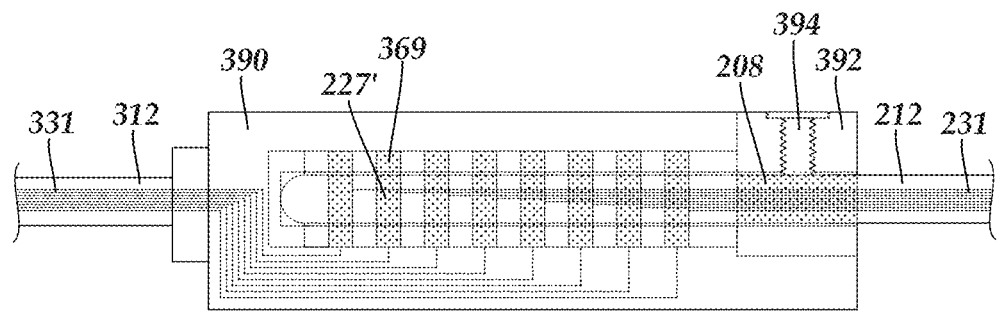
FIG. 4 is a schematic side view of one embodiment of the lead of FIG. 2 coupled to the lead extension of FIG. 3, according to the invention.

FIG. 4 shows, in schematic side view, one embodiment of the lead 212 received by the lead-extension connector 390. In the illustrated embodiment, the lead terminals 227, such as lead terminal 227', are aligned with the lead-extension connector contacts, such as lead-extension connector contact 369. Accordingly, the lead conductors 231 are electrically coupled with the lead-extension conductors 331. Additionally, in the illustrated embodiment the lead retention sleeve 208 is aligned with the lead-extension retention block 392 and the retaining member 394 is pressing the lead retention sleeve 208 against the lead-extension retention block to retain the lead 212 within the lead-extension connector 390.

Figure 5:
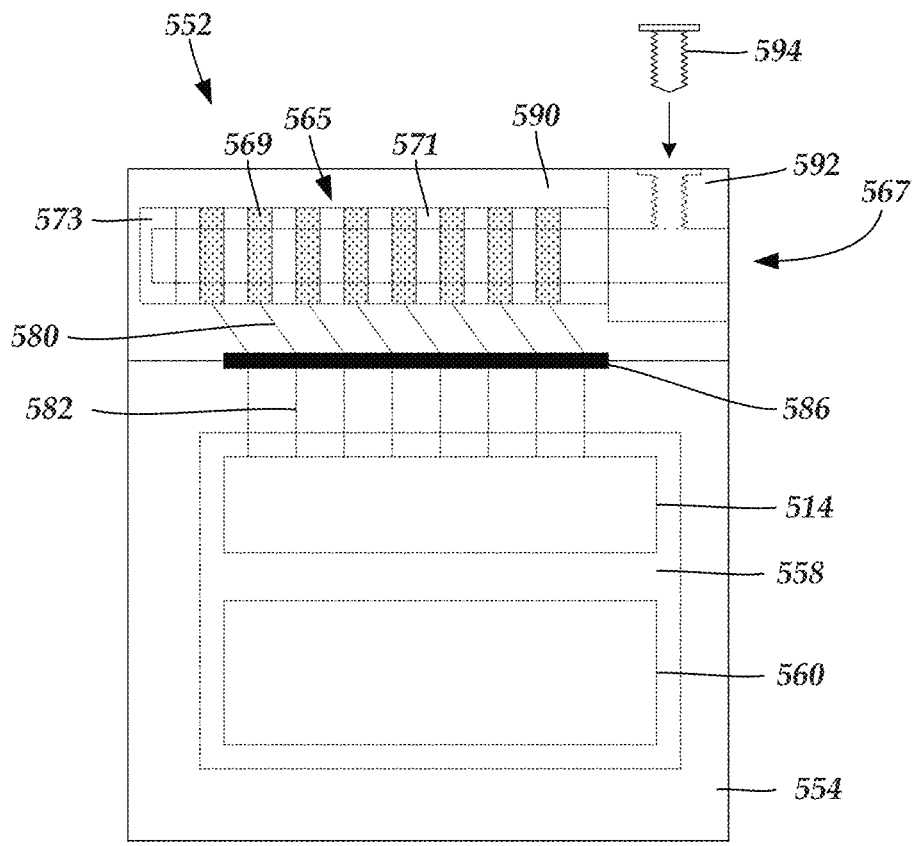
FIG. 5 is a schematic side view of one embodiment of a control module suitable for receiving either the lead of FIG. 2 or the lead extension of FIG. 3, according to the invention.

FIG. 5 shows, in schematic cross-sectional side view, one embodiment of a control module 552 suitable for coupling with an elongated member (e.g., the lead 212, the lead extension 312, or other intermediary device). The control module 552 includes a housing having a sealed portion 554 that houses an electronic subassembly 558 with a pulse generator 514 and, optionally, a power supply 560.

The housing further includes an unsealed portion that includes a connector 590 configured to receive an elongated device (e.g., the lead 212, the lead extension 312, or other intermediary device). Optionally, the connector 590 is positioned along an outer surface of the sealed portion of the housing. The connector 590 contains a connector stack 565 that defines a connector lumen 567 configured to receive the proximal portion of the elongated member. The connector stack 565 includes an array of connector contacts, such as connector contact 569, arranged along the connector lumen 567 and configured to electrically couple with terminals of the elongated member when the proximal portion of the elongated member is received by the connector 590. The connector contacts are electrically isolated from one another by electrically-nonconductive spacers, such as spacer 571. The connector stack may also include an end stop 573 to promote alignment of the elongated-member terminals with the connector contacts.

Feedthrough interconnects, such as feedthrough interconnect 582, are electrically coupled to the electrical subassembly 558 and extend within the sealed portion of the housing to a feedthrough interface 586 disposed along an interface between the sealed and unsealed portions of the housing. The connector contacts are electrically coupled to interconnect wires, such as interconnect wire 580, that extend along the unsealed portion of the housing and electrically couple the connector contacts to the feedthrough interconnects at the feedthrough interface 586. In some embodiments, the connector 590 is positioned along an outer surface of the sealed housing over the feedthrough interface 586. In other embodiments, the connector 590 is disposed at least partially within an outer surface of the sealed housing.

The connector 590 further includes a retention assembly for facilitating retention of the proximal portion of the elongated member when the proximal portion of the elongated member is received by the control module 552. In the illustrated embodiment, the retention assembly includes a retention block 592. The retention block 592 is positioned to align with the retention sleeve (208 in FIG. 2; 308 in FIG. 3) of the elongated member when the elongated member is received by the control module 552. In the illustrated embodiment, the retention assembly further includes a retaining member (e.g., a set screw, a pin, or the like) 594 for pressing the retention sleeve of the inserted elongated member against the retention block to retain inserted elongated member within the control module 552.

Figure 6:
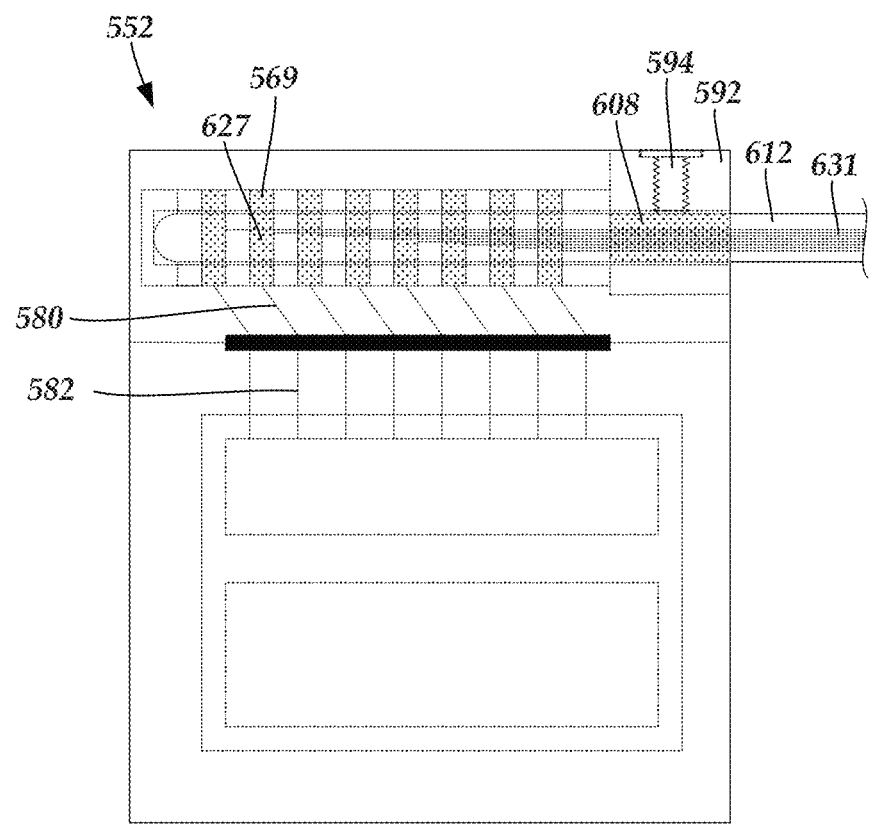
FIG. 6 is a schematic side view of one embodiment of an elongated member retained by the control module of FIG. 5, according to the invention.

FIG. 6 shows, in schematic side view, one embodiment of an elongated member 612 (e.g., the lead 212, the lead extension 312, or other intermediary device) received by the control module 552. In the illustrated embodiment, the elongated-member terminals, such as elongated-member terminal 627, are aligned with the connector contacts, such as connector contact 569. Accordingly, the elongated-member conductors 631 are electrically coupled with the interconnect wires 580 and feedthrough interconnects 582. Additionally, in the illustrated embodiment an retention sleeve 608 disposed along the elongated member 612 is aligned with the retention block 592 and the retaining member 594 is pressing the elongated-member retention sleeve 608 against the retention block to retain the elongated member 612 within the control module 552.

Figure 7:
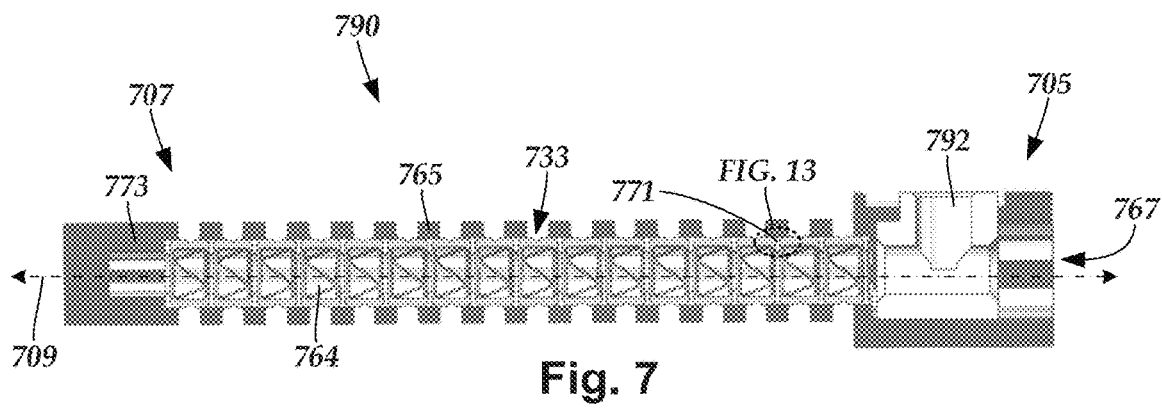
FIG. 7 is a schematic longitudinal cross-sectional view of one embodiment of a connector suitable for receiving a lead or lead extension, according to the invention.

Turning to FIG. 7, in at least some conventional electrical stimulation systems coupling a neuromodulation lead to a lead extension or coupling a lead or lead extension to an implantable pulse generator (IPG) header is accomplished using canted coil spring contacts, cantilevered leaf springs, or contact rings with ball-spring assemblies disposed within the IPG header.

An alternative assembly for electrically coupling a lead or lead extension to a connector, described below, includes contacts formed from electrically conductive wires configured into a series of bends separated from one another by contact regions. The bends of the wire are disposed in a contact housing in a configuration that enables portions of the wire to span a connector lumen and physically contact leads or lead extensions inserted into the connector lumen. The physical contact by the received lead or lead extension causes the contact regions of the wire to flex radially outward and remain in physically contact with the lead or lead extension.

The alternative assembly for electrically coupling a lead or lead extension to a connector may enable a reduction in a radial dimension of contacts from conventional connector assemblies. A reduced radial dimension may enable either a reduction in size from conventional connectors, or an increase in the amount of space available for other components.

Additionally, the alternative assembly may enable a reduced length for each contact along a longitudinal axis of the connector from conventional connector assemblies. A reduced length may potentially enable an increase in the contacts along a connector lumen and, in turn, a corresponding increase in the number of terminals along a lead or lead extension suitable for insertion into a single connector lumen within the connector, as compared to conventional electrical stimulation systems.

Furthermore, the alternative assembly may reduce an insertion force needed for insertion of a lead or lead extension into the connector, as compared to conventional connector assemblies. In at least some embodiments, the alternative assembly may also enable insertion of a lead or lead extension along opposing directions of a connector lumen.

FIG. 7 shows, in schematic longitudinal cross-sectional view, one embodiment of a connector 790 suitable for receiving an elongated member (e.g., the lead 212, the lead extension 312, or other intermediary device). The connector 790 is suitable for disposing along a control module, a lead extension, or other intermediary device.

The connector 790 includes a connector body 765 having an elongated shape with a first end 705, an opposing second end 707, and a longitudinal axis 709. The connector body defines a port 767 at the first end 705 configured for receiving the elongated member. Contact assemblies, such as contact assembly 733, are axially spaced-apart from one another within the connector body. Seals, such as seal 771, are optionally disposed within the connector body 765 between the contact assemblies 733. The connector assemblies (and optional seals) collectively form a lumen 764 that extends from the port 767 along the longitudinal axis 709 of the connector body. The lumen 764 is configured to receive the elongated member when the elongated member is inserted into the port. The contact assemblies are described below, with reference to FIGS. 8A-12B. The seals are described thereafter, with reference to FIGS. 13-14B.

The connector 790, optionally, includes a retention assembly for facilitating retention of the proximal portion of the elongated member when the proximal portion of the elongated member is received by connector 790. In the illustrated embodiment, the retention assembly includes a retention block 792. The retention block 792 is positioned to align with a retention sleeve (see e.g., 208 in FIG. 2) of the elongated member when the elongated member is received by the control module 552. In the illustrated embodiment, the retention assembly further includes a retaining member (e.g., a set screw, a pin, or the like) for pressing the retention sleeve of the inserted elongated member against the retention block to retain inserted elongated member within the connector 790. The connector stack may also include an end stop 773 to promote alignment of the elongated-member terminals with the contact assemblies.

Figure 8A:
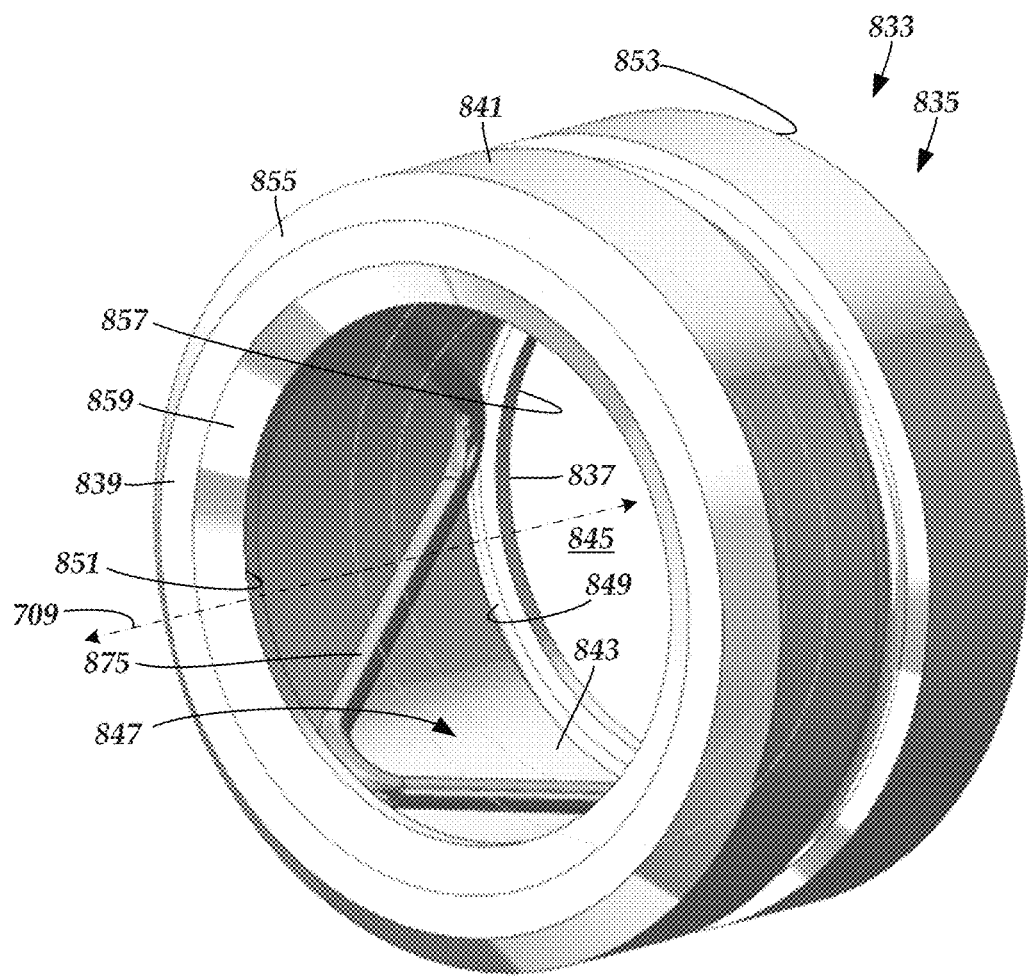
FIG. 8A is a schematic perspective view of one embodiment of a contact assembly suitable for disposing in the connector of FIG. 7, the contact assembly including a spring contact disposed in a pocket defined along an inner circumferential surface of a contact housing, according to the invention.
Figure 8B:
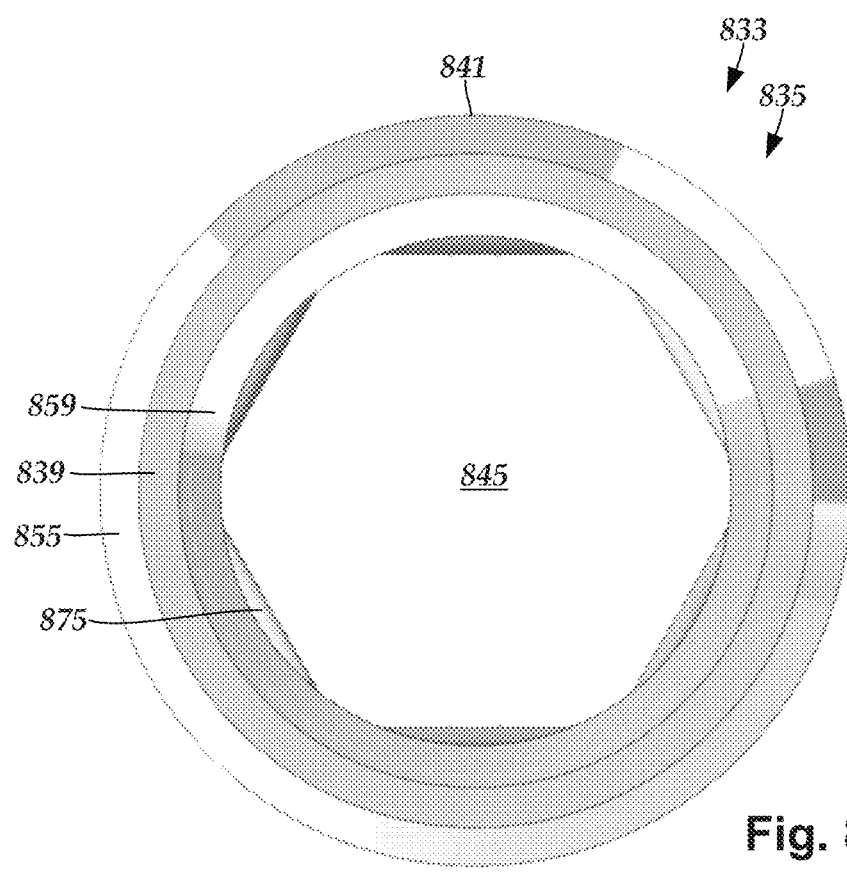
FIG. 8B is a schematic side view of one embodiment of the contact assembly of FIG. 8A, according to the invention.
Figure 8D:
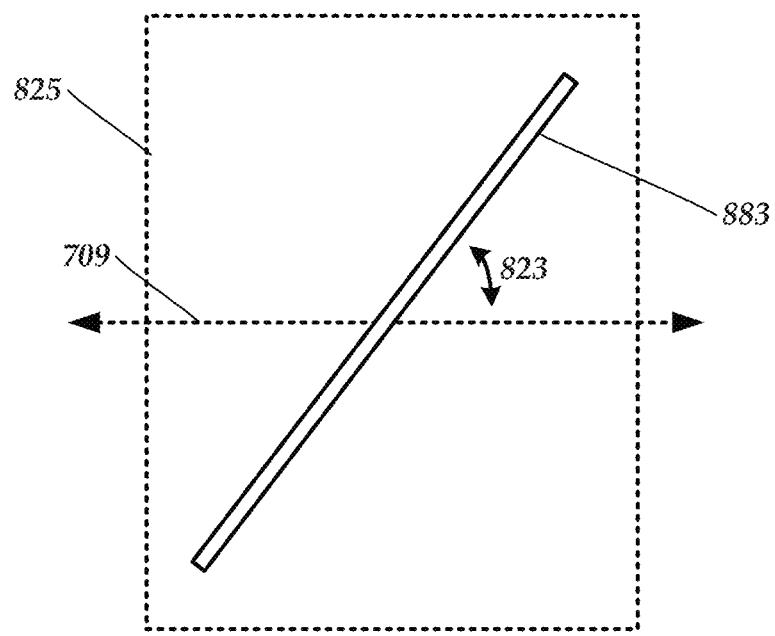
FIG. 8D is a schematic illustration of the angling of a spring contact relative to a longitudinal axis of the connector, according to the invention.
Figure 8C:
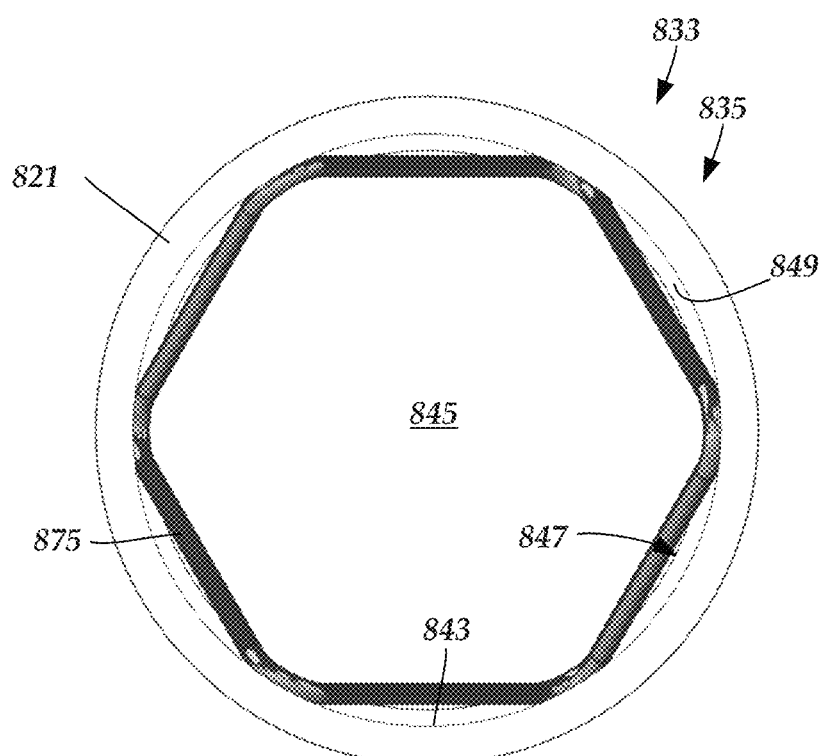
FIG. 8C is a schematic, transverse cross-sectional view of one embodiment of the contact assembly of FIG. 8A, according to the invention.

FIG. 8A shows, in schematic perspective view, one embodiment of a contact assembly 833 suitable for use with the connector 790. FIG. 8B shows the contact assembly 833 in side view. FIG. 8C shows the contact assembly 833 in transverse cross-sectional view. The contact assembly 833 includes a contact housing 835 having a first sidewall 837, an opposing second sidewall 839, and an outer circumferential surface 841 extending between the first and second sidewalls 837, 839, respectively. The outer circumferential surface 841 can have any suitable shape. In the illustrated embodiments, the outer circumferential surface 841 is shown as having a round transverse profile. It will be understood that the transverse dimension is transverse to the longitudinal axis (709 in FIG. 7) of the connector. It is noted that the longitudinal axis 709 is also the longitudinal axis of the contact assembly.

An inner circumferential surface 843 also extends between the first and second sidewalls and forms an aperture 845 that, in turn, forms at least a portion of the lumen (764 in FIG. 7). The inner circumferential surface 843 can have any suitable shape. In the illustrated embodiments, the inner circumferential surface 843 is shown as having a round transverse profile. The contact housing 835 can have any suitable shape. In the illustrated embodiments, the contact housing is shown as being cylindrical, or ring-shaped, with the sidewalls 837, 839 extending along planes transverse to the longitudinal axis 709.

In at least some embodiments, outer circumferential chamfers 853, 855 define an edge extending between the sidewalls 837, 839, respectively, and the outer circumferential surface 841. In at least some embodiments, inner circumferential chamfers 857, 859 define an edge extending between the sidewalls 837, 839, respectively, and the inner circumferential surface 843. As discussed in more detail below, with reference to FIGS. 13-14B, one or more of the chamfers 853, 855, 857, 859 may be useful for providing space for one or more portions of one or more seals (771 in FIG. 7) disposed between adjacent contact housings.

The inner circumferential surface 843 defines a pocket 847 extending around at least half of a circumference of the inner circumferential surface 843. In at least some embodiments, the pocket 847 extends around at least three-fourths of the circumference of the inner circumferential surface 843. In at least some embodiments, the pocket 847 extends around the entire circumference of the inner circumferential surface 843.

The inner circumferential surface 843 is bound on opposing sides of the contact housing by a first interior surface 849 of the first sidewall 837 and a second interior surface 851 of the second sidewall 839. A spring contact 875 is disposed in the pocket 847. The spring contact 875 is bent into a configuration such that, when disposed in the pocket of a contact housing, portions of the spring contact extend into the aperture and are, therefore, exposed to the lumen (764 in FIG. 7) and physically contacted by an elongated member when the elongated member is inserted into the port (767 in FIG. 7) and extended along the lumen.

The contact housings can be formed from any biocompatible material suitable for implantation and stiff enough to resist deformation by elongated members when elongated members are inserted through the apertures 845 of the contact housings. The contact housings are also formed from materials that are stiff enough to retain the spring contact in the pocket while the spring contact is in a compressed, strained configuration.

The spring contact 875 contains one or more contact regions 883 which are optionally coupled together by one or more bends 881. The contact regions 883 are not parallel to the longitudinal axis 709 of the connector, but extend diagonally, and are angled, with respect to the longitudinal axis 709 of the connector (and the contact assembly). FIG. 8D illustrates one example of a contact region 883. If the contact region 883 is straight, a plane 825 can be defined by the contact region 883 and the longitudinal axis 709 of the connector. Prior to insertion of the lead or lead extension, the contact region 883 forms an angle 823 with respect to the longitudinal axis 709. In at least some embodiments, the angle 823 is in a range of 20 to 70 degrees or in a range of 30 to 60 degrees. If the contact region 883 is bent, an angle 823 can still be determined or defined by, for example, a plane 825 defined by the longitudinal axis 709 and a line having an instantaneous slope (e.g., first derivative) at a selected point on the contact region 883 (e.g., the center of contact region). It is believed that the angling of the contact region 883 relative to the longitudinal axis 709 of the connector can reduce the insertion force for inserting a lead into the connector.

Figure 9A:
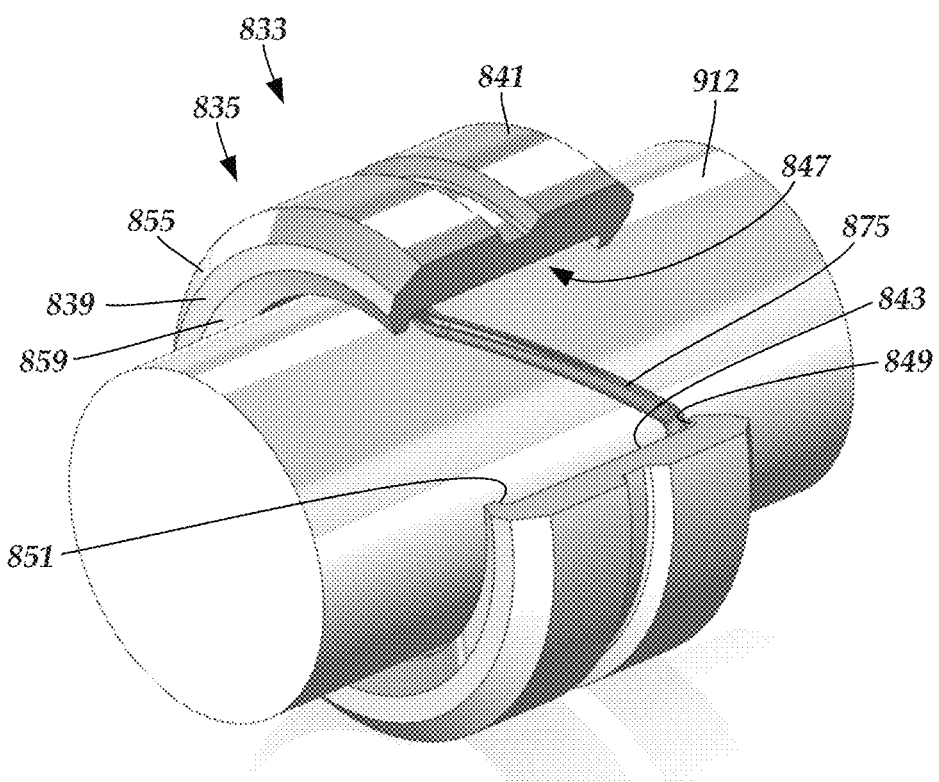
FIG. 9A is a schematic perspective view of one embodiment of a portion of a lead extending through an aperture defined by the inner circumferential surface of the contact assembly of FIG. 8A and physically contacting the spring contact of the contact assembly, according to the invention.
Figure 9B:
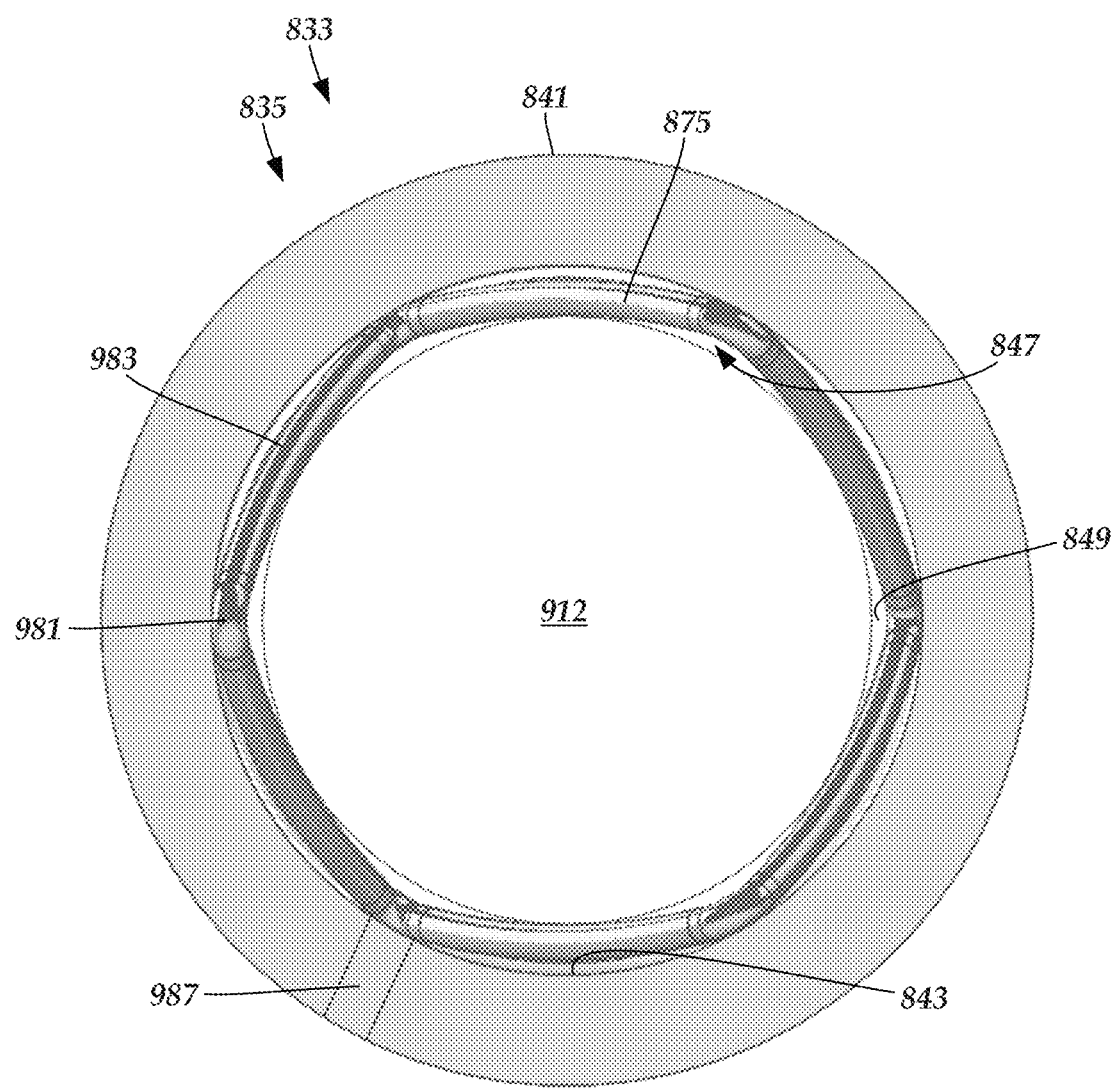
FIG. 9B is a schematic, transverse cross-sectional view of one embodiment of the lead and contact assembly of FIG. 9A, according to the invention.
Figure 10A:
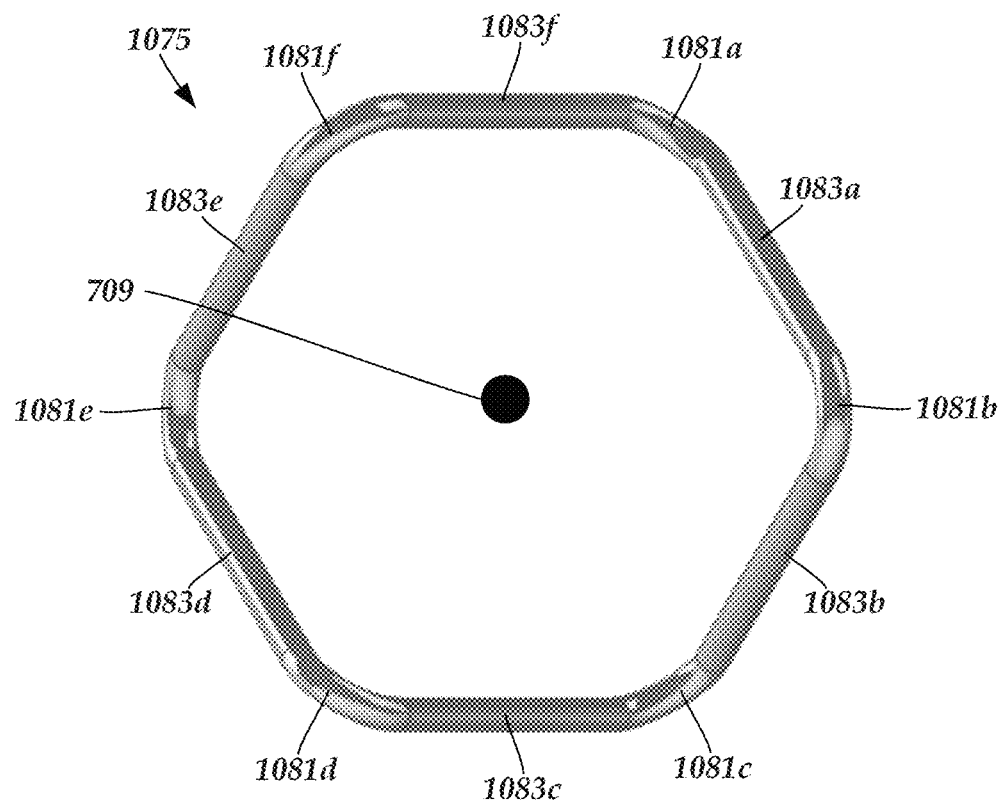
FIGS. 10A-10D are schematic views of the spring contact of FIG. 8A, as seen from several different angles, according to the invention.
Figure 10B:
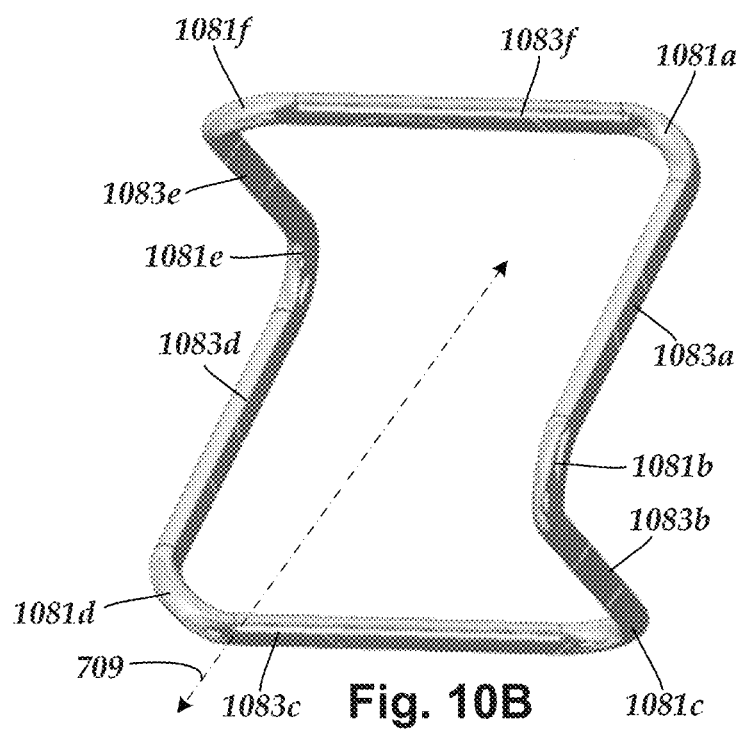
Figure 10C:
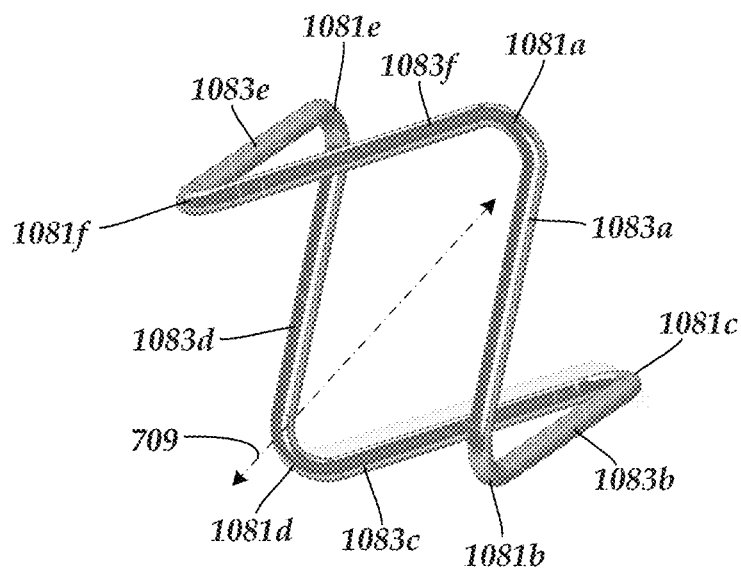
Figure 10D:
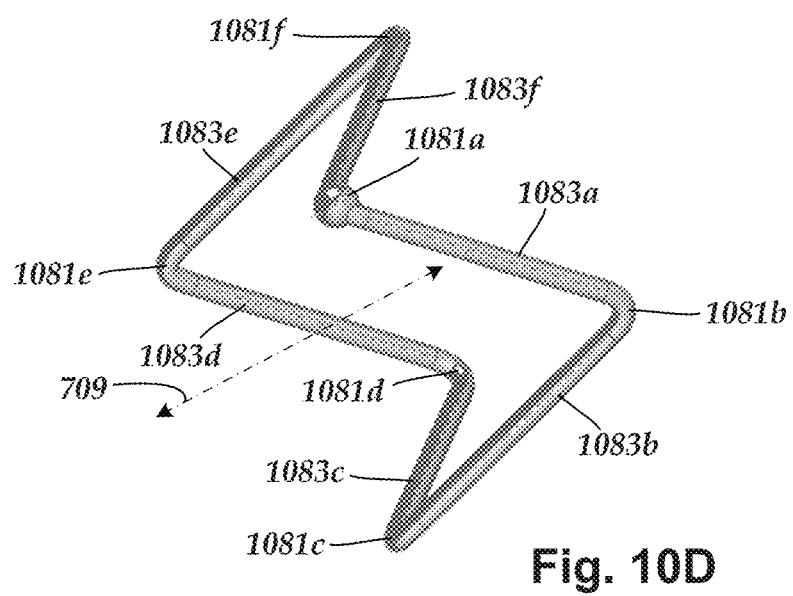

FIG. 9A shows, in schematic perspective view, one embodiment of a portion of a lead 912 extending through the aperture 845 of the contact assembly 835 and physically contacting the spring contact 875 disposed in the pocket 843 of the contact assembly. FIG. 9B shows the lead 912 and the contact assembly 835 in transverse cross-sectional view.

The spring contact 875 is formed from an electrically-conductive wire shaped to include multiple bends, such as bend 981. The bends 981 are separated from one another by contact regions, such as contact region 983. As shown in FIG. 9A, the spring contact 875 is configured such that, when the spring contact 875 is inserted into the pocket 847 of the contact housing 835, the spring contact 875 is in a compressed (strained) configuration with the bends urged against the opposing side surfaces of the pocket (i.e., the interior surfaces of the sidewalls). Accordingly, the contact regions 983 of the spring contact crisscross the pocket 847.

The contact regions 983 are configured to extend into the aperture 845 of the contact housing as they extend diagonally across (i.e., crisscross) the arced pocket between the interior surfaces 849, 851 of the sidewalls. Accordingly, the contact regions are exposed to the lumen of the connector and physically contact one or more terminals of an elongated member when the proximal end of the elongated member is inserted into the port (767 in FIG. 7) and extended along the lumen (764 in FIG. 7). As shown in FIGS. 8A and 9A, the contact regions 983 extend across the arced pocket 847 diagonally with respect to the longitudinal axis 709 of the connector body 765 and are circumferentially spaced-apart from one another around a circumference of the inner circumferential surface 843.

The physical contact between the lead or lead extension and the contact regions urges the contact regions to flex radially outward into the pocket 847. This produces a bending deflection of the contact regions. In at least some embodiments, the outward radial flexing (or bending deflection) of the contact regions urges at least one of the bends 981 to slide circumferentially along the pocket 847. Accordingly, in at least some embodiments at least one bend of the bent wire is not affixed to the pocket.

In some embodiments, opposing ends of the bent wire are attached together (e.g., welded, tied, epoxied, or the like). In other embodiments, the opposing ends of the bent wire are not attached together. In at least some embodiments, the opposing ends of the bent wire are configured to move independently from one another when the bent wire is contacted by a received elongated member. In at least some embodiments, at least one end of the bent wire is affixed to the contact housing. In at least some embodiments, the bent wire is affixed to the contact housing along one or more bends. In at least some embodiments, the bent wire is affixed to the contact housing along one or more ends. In at least some embodiments, the bent wire is not affixed to the contact housing. In at least some embodiments, the bent wire is maintained within the pocket of the contact housing solely by the spring force of the spring contact causing the bends to press against the opposing interior surfaces of the sidewalls.

The spring contacts 875 are electrically coupled to other conductors (e.g., interconnects disposed within a control module, lead-extension conductors disposed within a lead extension, or the like). In at least some embodiments, an aperture (e.g., aperture 987 of FIG. 9B) extends through the contact housing from the outer circumferential surface 841 to the inner circumferential surface 843 and is sufficient for providing access for electrically coupling the spring contact 875 to other conductors that are external to the contact housing.

The contact housing can be electrically conductive, electrically nonconductive, or include both electrically-conductive portions and electrically-nonconductive portions. In embodiments where the contact housing is electrically conductive, the spring contact can be electrically coupled to one or more conductors disposed external to the contact housing by electrically coupling the external conductor(s) to the outer circumferential surface 841 of the contact housing.

In at least some embodiments, the spring contact is not a coil, although, in some embodiments, the spring contact can form a single loop. In at least some embodiments, the spring contact is made of wire and is not a coil with a coil diameter greater than the diameter of the wire (although the wire may be made of coiled filars.) In at least some embodiments, the spring contact is sized to fit in the pocket while in a compressed configuration and make one revolution, or approximately one revolution (within 30 degrees, 25 degrees, 20 degrees, 15 degrees, 10 degrees, or 5 degrees of one revolution), of the pocket with a desired number of bends (and corresponding contact regions crisscrossing the pocket). In at least some embodiments, the spring contact is a straight wire or the contact region(s) of the spring contact are straight. In other embodiments, the spring contact or the contact region(s) of the spring contact are slightly bent (e.g., form an angle between ends of the spring contact or contact region of no more than 20, 15, 10, 5, or fewer degrees.

In some embodiments, the spring contact is formed as a continuous loop of material. FIG. 10A-10D are schematic views of a spring contact 1075, as seen from different angles. The illustrated spring contact 1075 includes bends 1081a-1081f and contact regions 1083a-1083f positioned between the bends. The bends include a first set of bends and a second set of bends, where each contact region extends between one bend from the first set of bends and one bend from the second set of bends. In FIGS. 10A-10D the first set of bends includes bends 1081a, c, e and the second set of bends includes bends 1081b, d, f.

As shown in FIGS. 10A-10D, the bends are arranged such that the contact regions 1083a-1083f do not all extend along a common plane. Instead, the contact regions 1083a-1083f extend along multiple different planes, thereby creating a three-dimensional aspect to the spring contact. The first set of bends are configured to bend in opposing directions from the second set of bends with respect to a plane extending through each of the contact regions 1083a-1083f and transverse to the longitudinal axis 709.

In at least some embodiments, the first set of bends (bends 1081a, c, e) are located along a first plane and the second set of bends (bends 1081b, d, f) are located along a second plane. In other words, in at least some embodiments the spring contact 1075 is capable of being laid upon a flat surface with either the first or second set of bends (either bends 1081a, c, e or bends 1081b, d, f) physically contacting the surface, and with the other of the first or second set of bends (as well as the contact surfaces) not physically contacting the surface. In at least some embodiments, the first plane and the second plane are parallel to one another. In at least some embodiments, the first plane and the second plane are each transverse to the longitudinal axis.

The spring contact 1075 is configured such that when the spring contact is disposed in a pocket of a contact assembly, the spring constant urges the first set of bends (bends 1081a, c, e) against either the first interior surface 849 of the first sidewall 837 or the second interior surface 851 of the second sidewall 839, while the second set of bends (bends 1081b, d, f) are urged against the other of the first interior surface 849 of the first sidewall 837 or the second interior surface 851 of the second sidewall 839. When the spring contact 1075 is disposed in the pocket of a contact housing, the alternating, opposing arrangement of the bends cause the contact regions 1083a-1083f to extend diagonally across the pocket with respect to the longitudinal axis 709 of the connector regardless of which of the two above configurations are implemented.

In the embodiments of the spring contact described above, the wire is shown having six bends. Other numbers of bends are contemplated including, for example, one, two, three, four, five, six, seven, eight, or more bends. In embodiments of the spring contact formed into a continuous loop of material (e.g., spring contact 1075), the spring contact includes at least three bends. In embodiments of the spring contact that are not formed as a continuous loop of material (see e.g., spring contact 1275, discussed below), the spring contact includes at least one bend.

The number of bends affects how far the contact regions extend into the aperture of the contact housing within which the spring contact is disposed. In at least some embodiments, the greater the number of bends, the less distance that each of the contact regions extend into the aperture of the contact housing. The number of bends also affects the number of contact regions circumferentially distributed around the pocket. In at least some embodiments, the greater the number of bends, the greater the number of contact regions. The amount of distance that the contact regions extend into the aperture, and the number of contact regions may affect how much insertion force is needed to insert an elongated member into the connector.

In at least some embodiments, the bends are equally spaced apart from one another along a length of the wire. In other embodiments, the bends are unequally spaced apart from one another along a length of the wire. In at least some embodiments, the bends each have equal angles. In other embodiments, the bends do not have each have equal angles. In at least some embodiments, when the spring contact is disposed in a contact housing the bends have equal angles along a plane transverse to the longitudinal axis 709 of the connector. In other embodiments, when the spring contact is disposed in a contact housing the bends have unequal angles along a plane transverse to the longitudinal axis 709 of the connector.

The spring contacts can be formed from any electrically conductive material suitable for implantation including, for example, MP35N, 80/10 PT-IR, or the like. The spring contacts can have any suitable transverse cross-section including, for example, round, oval, capsule-shaped, rectangular, or other geometric or nongeometric shape.

Figure 11A:
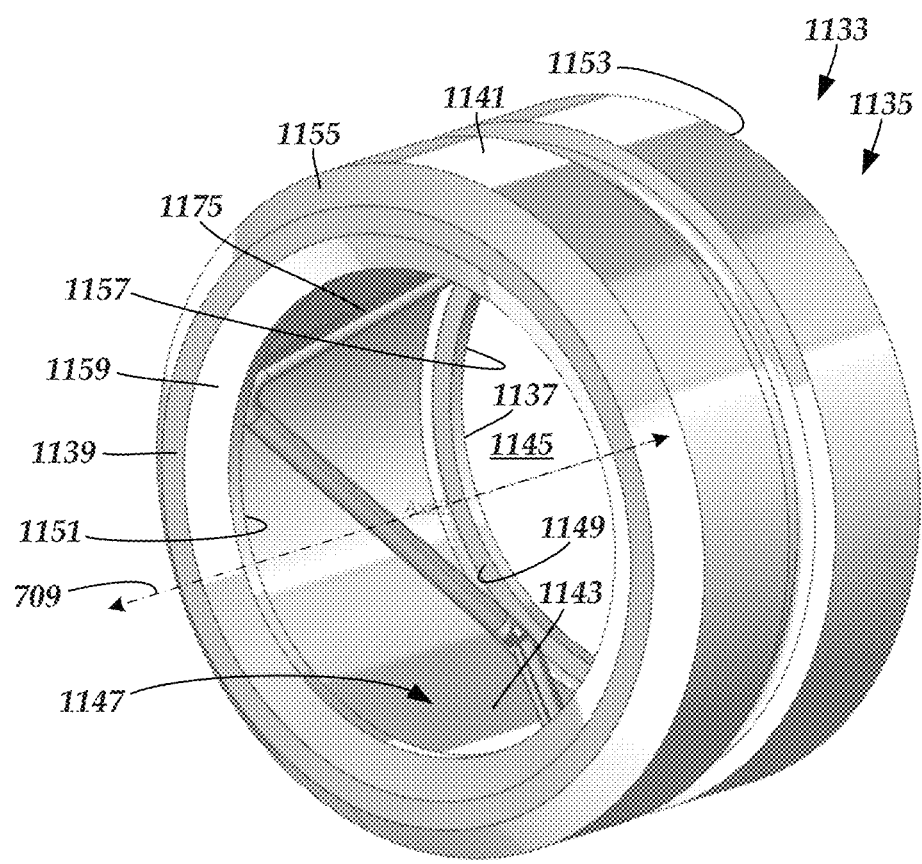
FIG. 11A is a schematic perspective view of another embodiment of a contact assembly that includes a spring contact disposed in a pocket defined along an inner circumferential surface of a contact housing, according to the invention.

Turning to FIG. 11A, the spring contacts shown in the previous figures include six bends. FIGS. 11A-12B show an alternate embodiment of a spring contact having five bends. Additionally, the spring contacts shown in the previous figures are formed either from a continuous loop of material or one or more pieces of material formed into a continuous loop. FIGS. 11A-12B show an alternate embodiment of a spring contact that does not form a continuous loop.

Figure 11B:
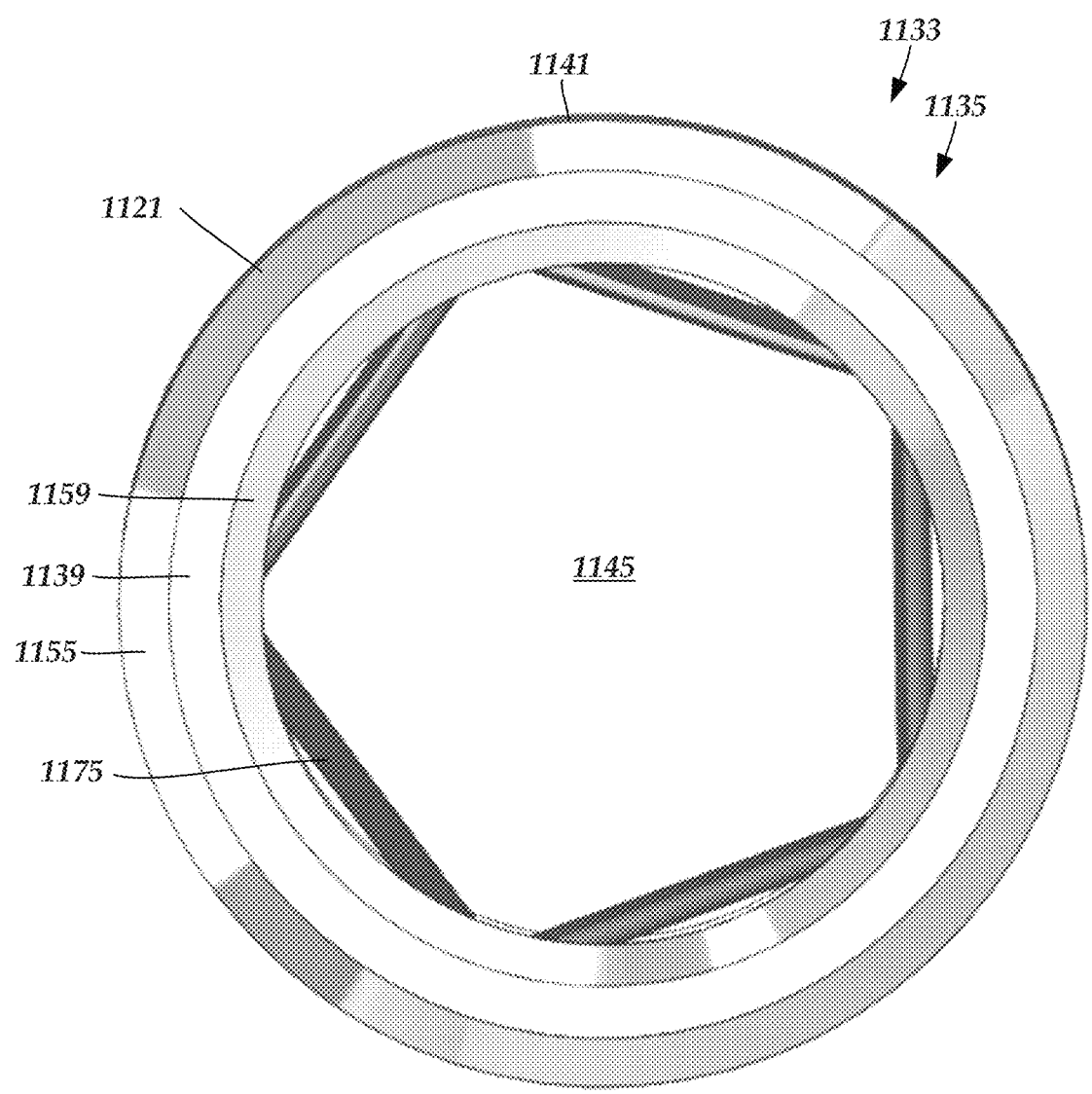
FIG. 11B is a schematic side view of one embodiment of the contact assembly of FIG. 11A, according to the invention.

FIG. 11A shows, in schematic perspective view, another embodiment of a contact assembly 1135. FIG. 11B shows the contact assembly 1135 in side view. The contact assembly 1135 includes a contact housing 1121 and a spring contact 1075. The contact housing 1121 is similar to the contact assembly 835, described above, and includes a first sidewall 1137, an opposing second sidewall 1139, and an outer circumferential surface 1141 extending between the first and second sidewalls 1137, 1139, respectively. An inner circumferential surface 1143 also extends between the first and second sidewalls and forms an aperture 1145 that, in turn, forms at least a portion of the lumen (764 in FIG. 7).

In at least some embodiments, optional outer circumferential chamfers 1153, 1155 define an edge extending between the sidewalls 1137, 1139, respectively, and the outer circumferential surface 1141. In at least some embodiments, optional inner circumferential chamfers 1157, 1159 define an edge extending between the sidewalls 1137, 1139, respectively, and the inner circumferential surface 1143. As discussed in more detail below, with reference to FIGS. 13-14B, one or more of the chamfers 1153, 1155, 1157, 1159 may be useful for providing space for one or more portions of one or more seals disposed between adjacent contact housings.

The inner circumferential surface 1143 defines a pocket 1147 extending around at least half of a circumference of the inner circumferential surface 1143. In at least some embodiments, the pocket 1147 extends around at least three-fourths of the circumference of the inner circumferential surface 1143. In at least some embodiments, the pocket 1147 extends around the entire circumference of the inner circumferential surface 1143.

The inner circumferential surface 1143 is bound on opposing sides of the contact housing by a first interior surface 1149 of the first sidewall 1137 and a second interior surface 1151 of the second sidewall 1139. A spring contact 1175 is disposed in the pocket 1147 and partially extends into the aperture 1145 of the contact housing. The spring contact 1175 is bent into a configuration such that, when disposed in the pocket of a contact housing, portions of the spring contact extending into the aperture are exposed to the lumen (764 in FIG. 7) and physically contact an elongated member when the elongated member is inserted into the port (767 in FIG. 7) and extended along the lumen.

The contact housings can be formed from any biocompatible material suitable for implantation and stiff enough to resist deformation by elongated members when elongated members are inserted through the apertures 1145 of the contact housings. The contact housings are also formed from materials that are stiff enough to retain the spring contact in the pocket while the spring contact is in a compressed, strained configuration.

Figure 12A:
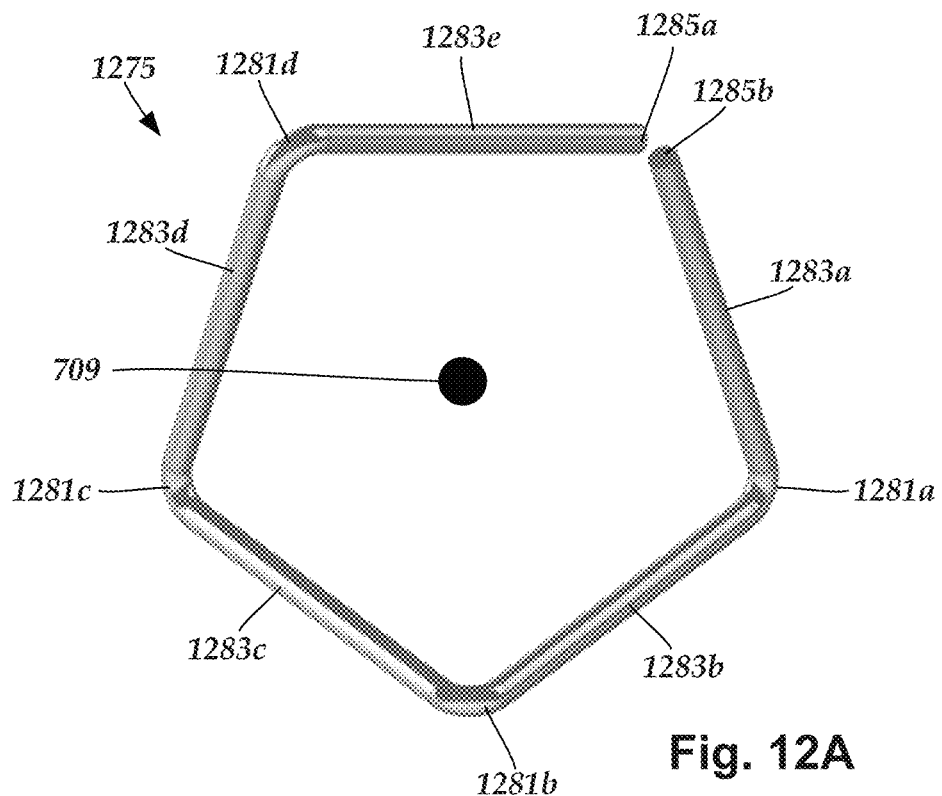
FIGS. 12A-12B are schematic views of the spring contact of FIG. 11A, as seen from several different angles, according to the invention.
Figure 12B:
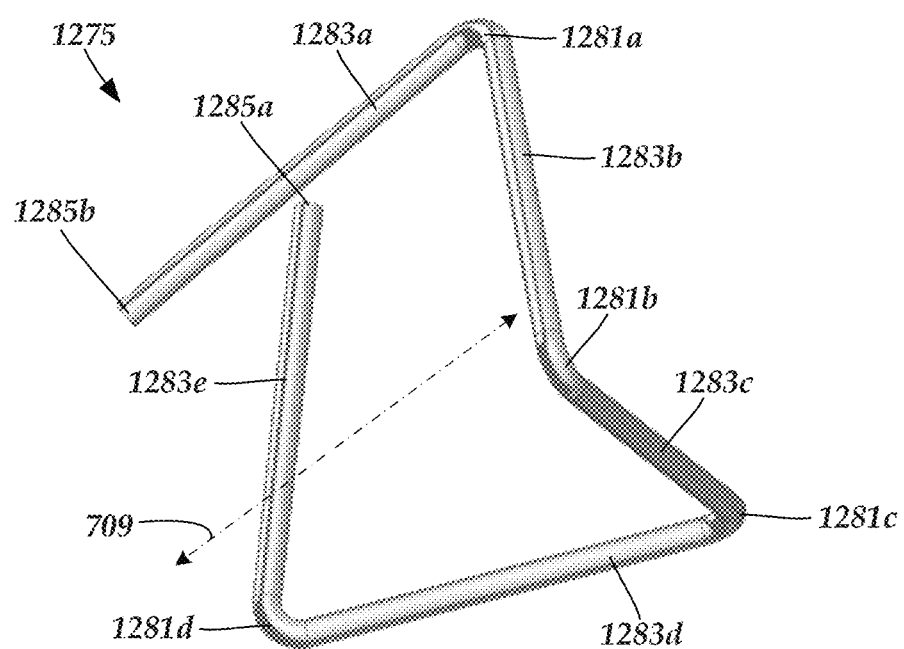

In some embodiments, the spring contact does not form a continuous loop of material. FIG. 12A-12B are schematic views of a spring contact 1275, as seen from several different angles. The illustrated spring contact 1275 includes bends 1281a-1281d and contact regions 1283a-e. The bends include a first set of bends and a second set of bends. In FIGS. 12A-12D the first set of bends includes bends 1281a, c and the second set of bends includes bends 1281b, d.

Unlike the previously-described spring contact 1075, the spring contact 1275 does not form a continuous loop of material. Instead, the spring contact 1275 includes a first end 1285a and an opposing second end 1285b that is not coupled to the first end 1285a. In at least some embodiments, at least one contact region extends between a bend from the first set of bends (bends 1281a, c) and one bend from the second set of bends (bends 1281b, d). In at least some embodiments, at least one contact region extends between a bend from the first set of bends (bends 1281a, c) and the second end 1285b. In at least some embodiments, at least one contact region extends between a bend from the second set of bends (bends 1281b, d) and the first end 1285a. In at least some embodiments, the wire includes a single bend and two contact regions, where one of the two contact regions is disposed between the bend and the first end, and the other of the two contact regions is disposed between the bend and the second end.

As shown in FIGS. 12A-12D, the bends are arranged such that the contact regions 1283a-1283e do not all extend along a common plane. Instead, the contact regions 1283a-1283e extend along multiple different planes, thereby creating a three-dimensional aspect to the spring contact. The first set of bends are configured to bend in opposing directions from the second set of bends with respect to a plane extending through each of the contact regions 1283a-1283e and transverse to the longitudinal axis 709.

In at least some embodiments, the first set of bends (bends 1281a, c) are located along a first plane and the second set of bends (bends 1281b, d) are located along a second plane. In at least some embodiments, the spring contact is configured with the first end 1285a also positioned along the first plane and the second end 1285b positioned along the second plane. In other words, in at least some embodiments the spring contact 1275 is capable of being laid upon a flat surface with either the first or second set of bends (either bends 1281a, c and, optionally, the first end 1285a; or bends 1281b, d and, optionally, the second end 1285b) physically contacting the surface, and with the other of the first or second set of bends (as well as the contact surfaces and, optionally, the other of the first or second end) not physically contacting the surface. In at least some embodiments, the first plane and the second plane are parallel to one another. In at least some embodiments, the first plane and the second plane are each transverse to the longitudinal axis.

The spring contact 1275 is configured such that when the spring contact is disposed in a pocket of a contact assembly, the spring constant urges the first set of bends (bends 1281*a, c* and, optionally, the first end 1285*a*) against either the first interior surface 849 of the first sidewall 837 or the second interior surface 851 of the second sidewall 839, while the second set of bends (bends 1281*b, d* and, optionally, the second end 1285*b*) are urged against the other of the first interior surface 849 of the first sidewall 837 or the second interior surface 851 of the second sidewall 839. When the spring contact 1275 is disposed in the pocket of a contact housing, the alternating, opposing arrangement of the bends cause the contact regions 1283*a*-1283*e* to extend diagonally across the pocket with respect to the longitudinal axis 709 of the connector regardless of which of the two above configurations are implemented.

Figure 16:
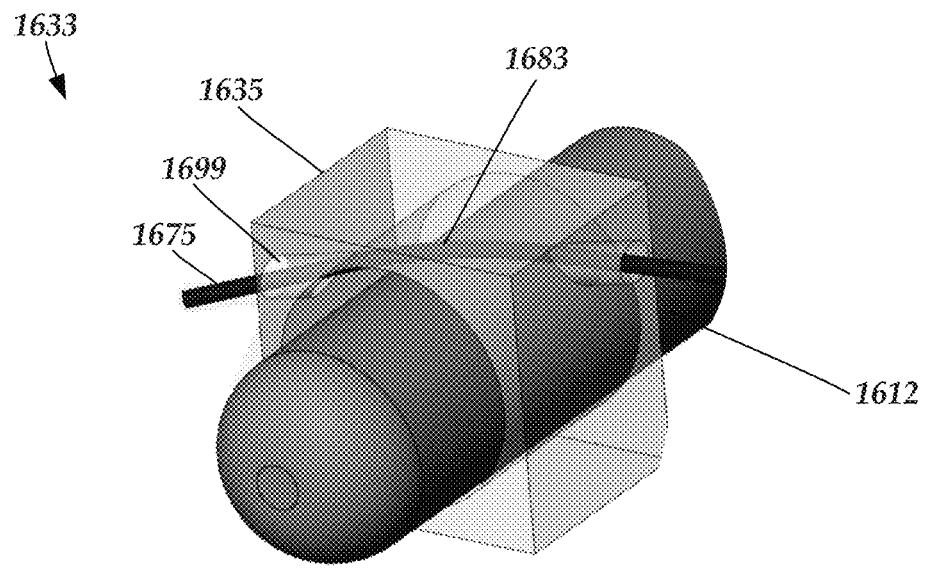
FIG. 16 is a schematic perspective view of another embodiment of a contact assembly, according to the invention.

FIG. 16 illustrates another embodiment of a contact assembly 1633 with a housing 1635, and a spring contact 1675 with a portion of a lead 1612 inserted into the contact assembly and deflecting a portion of the spring contact. As illustrated in this embodiment, the spring contact 1675 includes only a single contact region 1683 and no bends. Accordingly, a spring contact has one or more contact regions and, optionally, one or more bends. In the embodiment of FIG. 16, the ends of the spring contact 1675 exit the housing 1635 through an aperture 1699. One or both ends can be attached to, or function as, interconnector wires 580 (FIG. 6).

Figure 17:
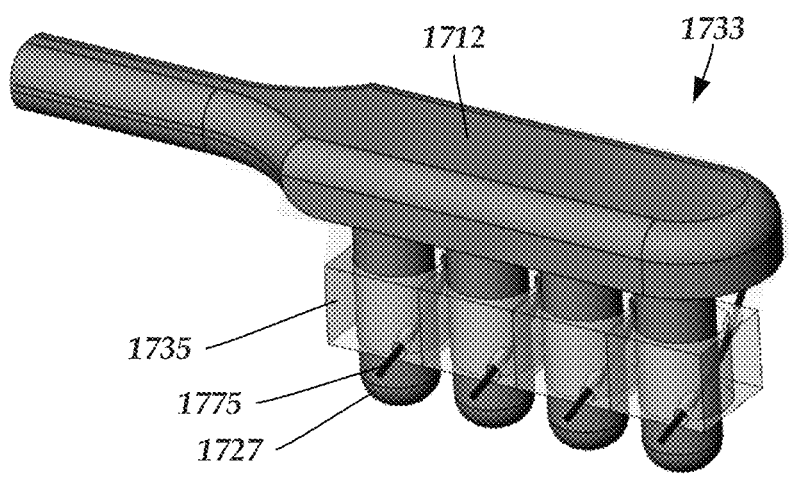
FIG. 17 is a schematic perspective view of one embodiment of a transverse array of contact assemblies, according to the invention.

The preceding connectors described above use axial arrays of contact assemblies. The spring contacts, however, can also be used for transverse arrays of contact assemblies. FIG. 17 illustrates a lead 1712 with a transverse arrangement of terminals, such as terminal 1727. A connector can include a transverse array of a contact assembly 1733 with spring contacts 1775 where the lumens of the individual contact assemblies are parallel to each other (although non-parallel arrangements can also be used.). It will be understood that any of the other spring contacts described above can also be used in a transverse array of contact assemblies. In this embodiment, the contact region of the spring contact 1775 forms an angle with the longitudinal axis of the contact assembly 1733, similar to that illustrated in FIG. 8D.

Figure 18:
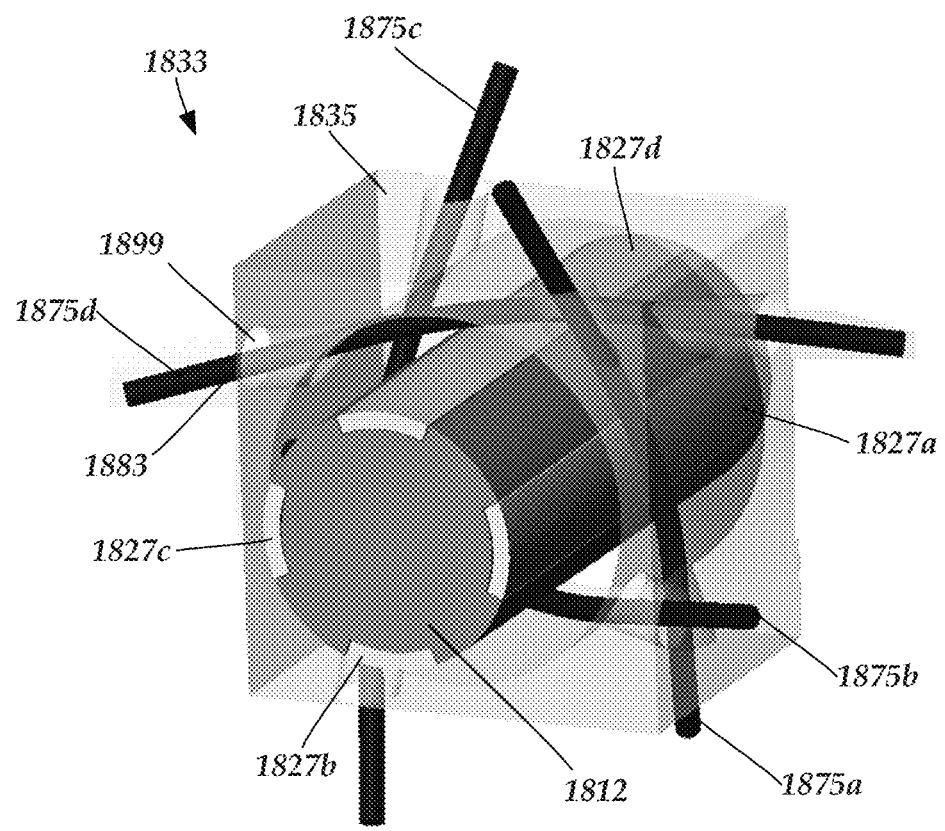
FIG. 18 is a schematic perspective view of an embodiment of a contact assembly for use with a lead having segmented electrodes, according to the invention.

Contact assemblies can also be formed for leads with segmented terminals. Examples of leads with segmented terminals can be found in U.S. Patent Applications Publications Nos. 2016/0129265; 2016/0129242; 2016/0228692; 2017/0014635; and 2017/0203104, all of which are incorporated herein by reference. FIG. 18 illustrates a portion of a lead 1812 with segmented terminals 1827*a*, 1827*b*, 1827*c*, 1827*d*. A contact assembly 1833 with a housing 1835 includes four spring contacts 1875*a*, 1875*b*, 1875*c*, 1875*d* which each contact only one of the segmented terminals 1827*a*, 1872*b*, 1827*c*, 1827*d*. The four spring contacts 1875*a*, 1875*b*, 1875*c*, 1875*d* are electrically isolated from each other. In the illustrated embodiment, each of the spring contacts 1875*a*, 1875*b*, 1875*c*, 1875*d* exits the housing 1835 through apertures 1899 similar to the embodiment illustrated in FIG. 16. It will be understood that arrangements with two, three, four, five, six, or more spring contacts can also be made.

Figure 13:
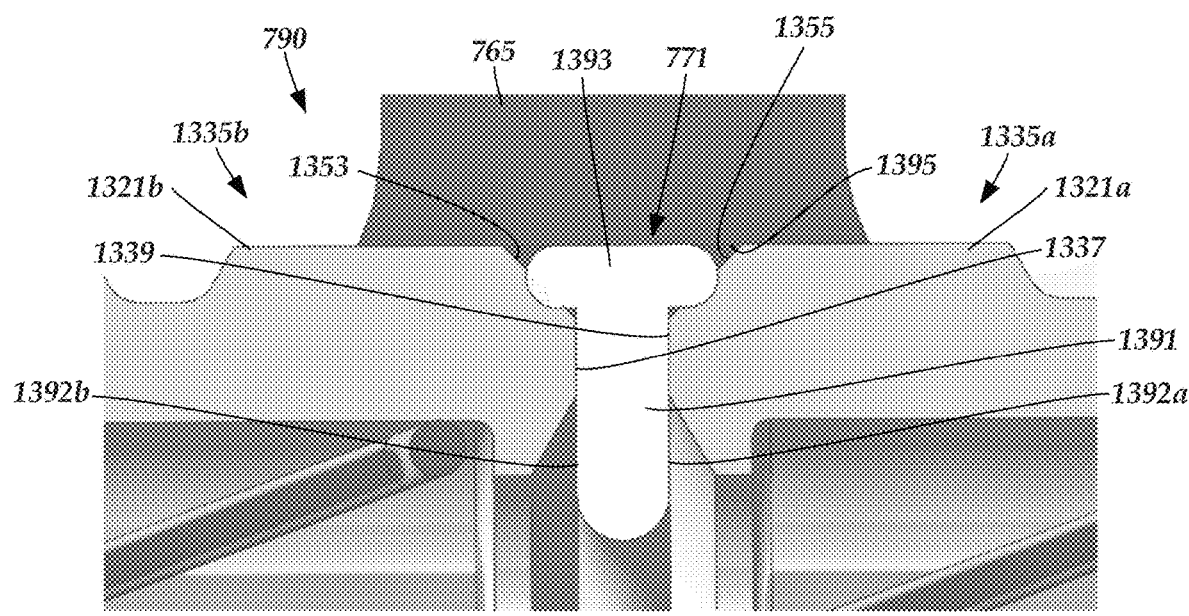
FIG. 13 is a schematic, close-up, longitudinal cross-sectional view of one embodiment of a portion of the connector of FIG. 7 that includes a seal disposed in the connector between two adjacent contact housings, according to the invention.
Figure 14A:
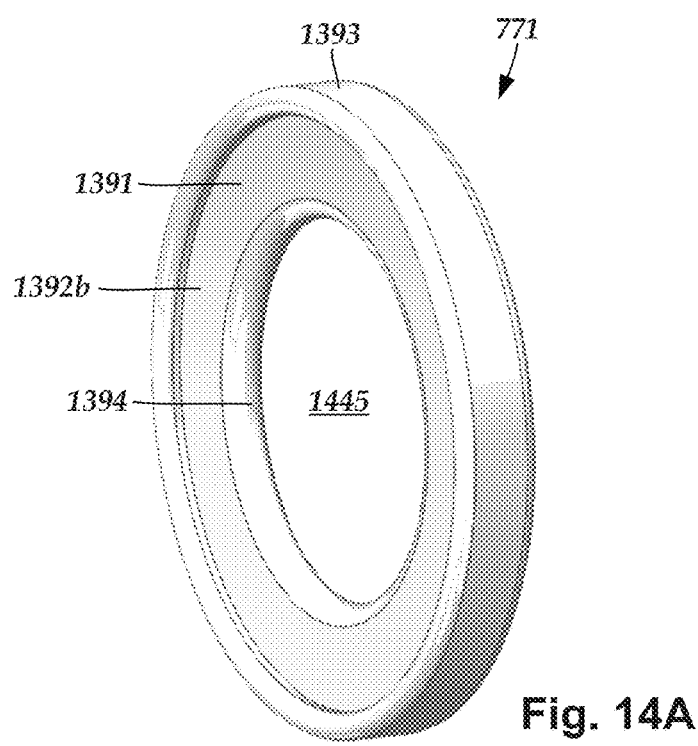
FIG. 14A is a schematic perspective view of one embodiment of the seal of FIG. 13, according to the invention.
Figure 14B:
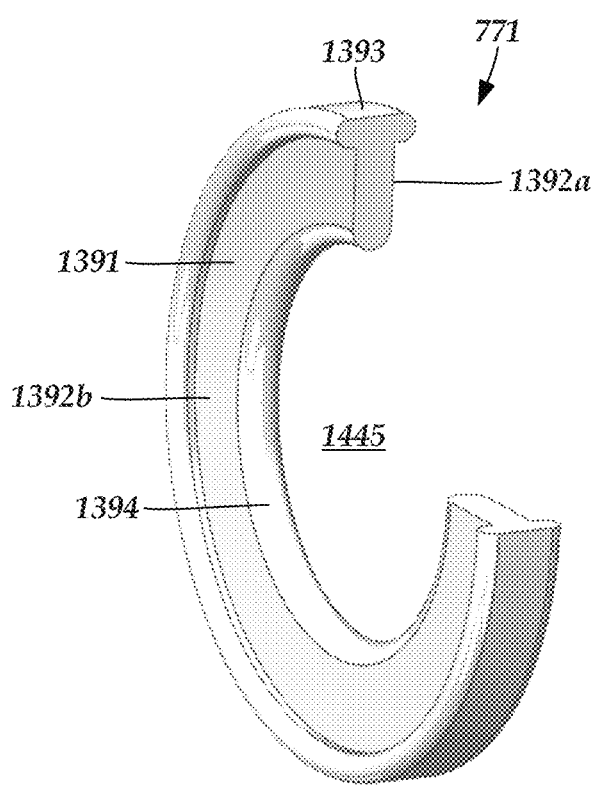
FIG. 14B is a schematic perspective view of one embodiment of the seal of FIG. 13 with a cutaway section showing a flange disposed along an outer circumferential surface of the seal, according to the invention.

Turning to FIGS. 13-14B, in at least some embodiments seals are disposed in the connector between axially-adjacent contact assemblies. Axial compression of the seals between the adjacent connector assemblies causes a radial expansion of the seals within cavities bounded by an inner surface of the connector body and the outer circumferential chamfers of the connector assemblies. The radial expansion of the seals within the cavities creates one or more seals within the connector.

FIG. 13 shows, in schematic longitudinal, cross-sectional view, one embodiment of a portion of the connector 790. The connector includes seals disposed between adjacent contact housings. FIG. 13 shows the seal 771 disposed in the connector body 765 between a first contact housing 1321*a* and a second contact housing 1321*b*. The seal 771 includes a washer-shaped seal body 1391 with a first major surface 1392*a* and an opposing second major surface 1392*b*. A flange 1393 is disposed along an outer circumference of the major surfaces 1392*a*, 1392*b*. The seal body 1391 is positioned between a second sidewall 1339 of the first contact housing 1321*a* and a first sidewall 1337 of the second contact housing 1321*b*. The flange 1393 is positioned in a cavity bounded by outer circumferential chamfers 1355, 1353 of the first and second contact housings 1321*a*, 1321*b*, respectively, and an inner circumferential surface 1395 of the connector body 765.

FIG. 14A shows, in schematic perspective view, one embodiment of the seal 771. FIG. 14B shows the seal 771 in perspective view with a portion of the seal body 1391 removed to more illustrate the flange 1393 in cross-section. The seal body 1391 includes an inner circumference 1394 that defines an aperture 1445 extending between the major surfaces 1392*a*, 1392*b* and which, when disposed in the connector, forms a portion of the lumen (764 in FIG. 7). In at least some embodiments, the seal body 1391 has a transverse profile that is the same as the transverse profile of the contact housings. In at least some embodiments, the seal body 1391 has a round transverse profile. The seal body 1391 is formed from an electrically-nonconductive, deformable material suitable for implantation (e.g., silicone rubber, or the like).

The flange 1393 extends around the outer circumference of the seal body 1391 and projects outwardly from at least one of the major surfaces 1392*a*, 1392*b*. The flange 1393 is formed from an electrically-nonconductive, deformable material suitable for implantation (e.g., silicone rubber, or the like).

When the seal is disposed between two connector housings along the longitudinal length of the connector, axial compression of the seal body by the flanking connector housings is converted to radial expansion. The radial expansion causes a sealing pressure by the flange against the surfaces positioned about the flange. As shown in FIG. 13, the flange is positioned along a tight cavity bounded by the inner surface 1395 of the connector body and the outer circumferential chamfers 1355, 1353 of the connector assemblies 1335*a*, 1335*b*, respectively. Consequently, axial compression of the seal body causes the flange to form a seal around the periphery of the cavity of the connector within which the contact assemblies are disposed.

Figure 15:
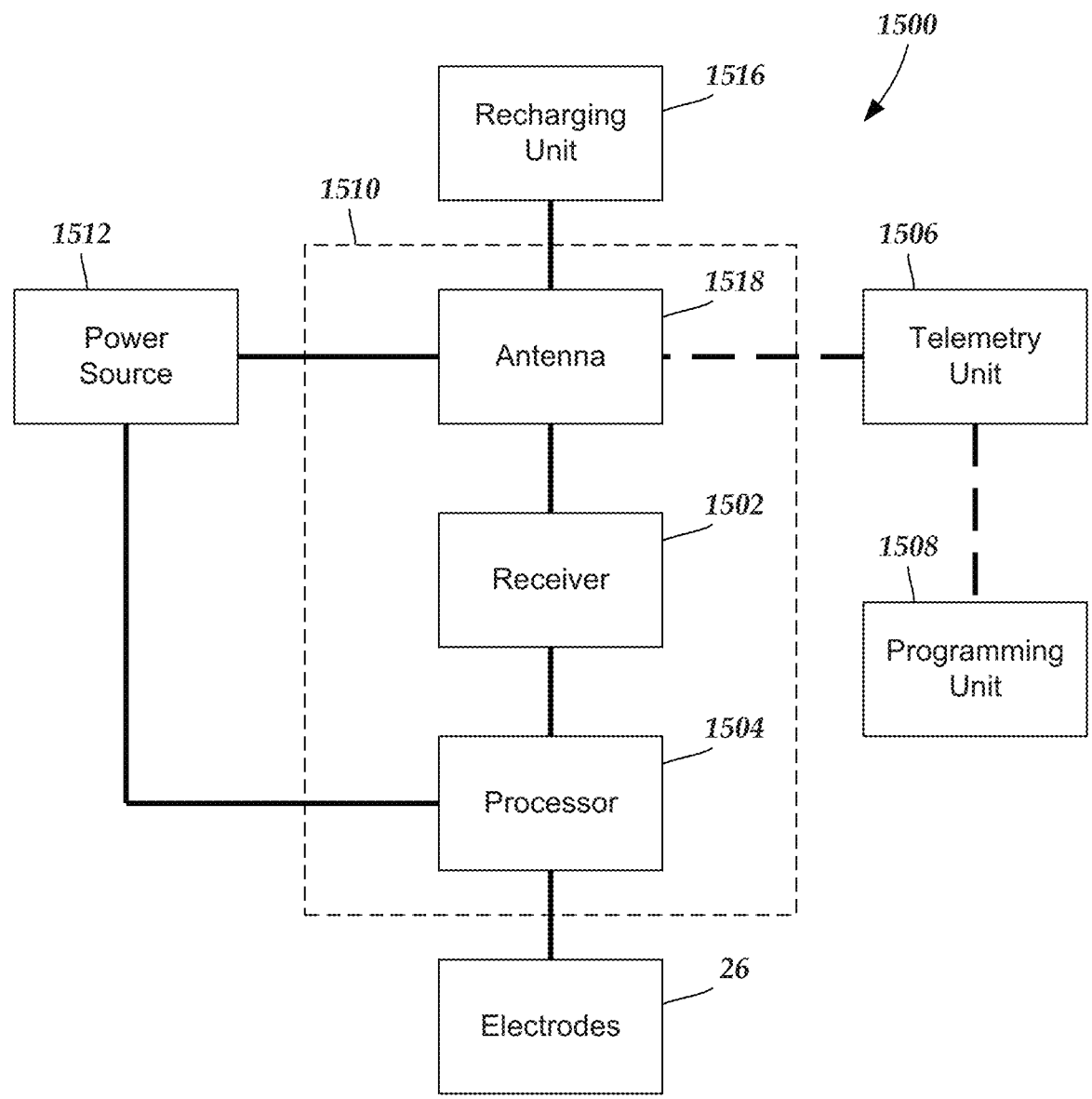
FIG. 15 is a schematic overview of one embodiment of components of an electrical stimulation system, according to the invention.

FIG. 15 is a schematic overview of one embodiment of components of an electrical stimulation system 1500 including an electronic subassembly 1510 disposed within a control module. It will be understood that the electrical stimulation system can include more, fewer, or different components and can have a variety of different configurations including those configurations disclosed in the stimulator references cited herein.

Some of the components (for example, a power source 1512, an antenna 1518, a receiver 1502, and a processor 1504) of the electrical stimulation system can be positioned on one or more circuit boards or similar carriers within a sealed housing of an implantable pulse generator, if desired. Any power source 1512 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1518 or a secondary antenna. The external power source can be in a device that is mounted on the skin of the user or in a unit that is provided near the user on a permanent or periodic basis.

If the power source 1512 is a rechargeable battery, the battery may be recharged using the optional antenna 1518, if desired. Power can be provided to the battery for recharging by inductively coupling the battery through the antenna to a recharging unit 1516 external to the user. Examples of such arrangements can be found in the references identified above.

In one embodiment, electrical current is emitted by the electrodes 26 on the paddle or lead body to stimulate nerve fibers, muscle fibers, or other body tissues near the electrical stimulation system. The processor 1504 is generally included to control the timing and electrical characteristics of the electrical stimulation system. For example, the processor 1504 can, if desired, control one or more of the timing, frequency, strength, duration, and waveform of the pulses. In addition, the processor 1504 can select which electrodes can be used to provide stimulation, if desired. In some embodiments, the processor 1504 selects which electrode(s) are cathodes and which electrode(s) are anodes. In some embodiments, the processor 1504 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1508 that, for example, allows modification of pulse characteristics. In the illustrated embodiment, the processor 1504 is coupled to a receiver 1502 which, in turn, is coupled to the optional antenna 1518. This allows the processor 1504 to receive instructions from an external source to, for example, direct the pulse characteristics and the selection of electrodes, if desired.

In one embodiment, the antenna 1518 is capable of receiving signals (e.g., RF signals) from an external telemetry unit 1506 which is programmed by the programming unit 1508. The programming unit 1508 can be external to, or part of, the telemetry unit 1506. The telemetry unit 1506 can be a device that is worn on the skin of the user or can be carried by the user and can have a form similar to a pager, cellular phone, or remote control, if desired. As another alternative, the telemetry unit 1506 may not be worn or carried by the user but may only be available at a home station or at a clinician's office. The programming unit 1508 can be any unit that can provide information to the telemetry unit 1506 for transmission to the electrical stimulation system 1500. The programming unit 1508 can be part of the telemetry unit 1506 or can provide signals or information to the telemetry unit 1506 via a wireless or wired connection. One example of a suitable programming unit is a computer operated by the user or clinician to send signals to the telemetry unit 1506.

The signals sent to the processor 1504 via the antenna 1518 and the receiver 1502 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1500 to cease operation, to start operation, to start charging the battery, or to stop charging the battery. In other embodiments, the stimulation system does not include the antenna 1518 or receiver 1502 and the processor 1504 operates as programmed.

Optionally, the electrical stimulation system 1500 may include a transmitter (not shown) coupled to the processor 1504 and the antenna 1518 for transmitting signals back to the telemetry unit 1506 or another unit capable of receiving the signals. For example, the electrical stimulation system 1500 may transmit signals indicating whether the electrical stimulation system 1500 is operating properly or not or indicating when the battery needs to be charged or the level of charge remaining in the battery. The processor 804 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A connector assembly, comprising:
 a connector body having an elongated shape with a first end, an opposing second end, and a longitudinal axis, the connector body defining a port at the first end configured and arranged to receive a proximal portion of a lead or lead extension; and
 a plurality of contact assemblies axially spaced-apart within the connector body and collectively forming a lumen that extends from the port along the longitudinal axis of the connector body, each contact assembly comprising
 a contact housing, and
 a spring contact disposed within contact housing and having a contact region that extends diagonally with respect to the longitudinal axis of the connector body, wherein the contact region is positioned within the contact housing so that insertion of the proximal portion of the lead or lead extension into the contact housing results in a bending deflection of the contact region of the spring contact while maintaining contact between the contact region and the lead or lead extension.

2. The connector assembly of claim 1, wherein
 the contact housing comprises a first sidewall, an opposing second sidewall, an outer circumferential surface extending between the first and second sidewalls, and an inner circumferential surface also extending between, and inset from, the first and second sidewalls and forming a portion of the lumen, the inner circumferential surface defining a pocket bound by the first sidewall and the second sidewall, and
 the spring contact is disposed in the pocket and further comprises a first bend, a second bend, with the contact region extending between the first bend and the second bend, wherein the spring contact urges the first bend to press against the first sidewall and the second bend to press against an interior surface of the second sidewall.

3. The connector assembly of claim 2, wherein the contact region is configured and arranged to flex radially outward into the pocket when physically contacting a lead or lead extension received by the port and inserted into the lumen.

4. The connector assembly of claim 2, wherein at least one of the first bend or the second bend is configured and arranged to slide circumferentially along the pocket when the contact region flexes radially outward.

5. The connector assembly of claim 2, wherein at least one of the first bend or the second bend is attached to the pocket.

6. The connector assembly of claim 2, wherein the spring contact comprises at least two first bends and at least two second bends.

7. The connector assembly of claim 2, wherein the spring contact has a first end and an opposing second end, wherein the first end is urged to press against an interior surface of the first sidewall, and wherein the second end is urged to press against the interior surface of the second sidewall.

8. The connector assembly of claim 1, wherein the spring contact is formed as a continuous loop of material.

9. The connector assembly of claim 1, wherein the plurality of contact assemblies comprises a first contact assembly and a second contact assembly, and further comprising a seal disposed between the first contact assembly and the second contact assembly.

10. A lead assembly, comprising:
a lead or a lead extension having a proximal portion and a distal portion, wherein the proximal portion of the lead or the lead extension comprises a plurality of terminals electrically insulated from one another; and
the connector assembly of claim 1.

11. An electrical stimulating system comprising:
the lead assembly of claim 10; and
a control module coupled to the lead assembly, the control module comprising
a housing, and
an electronic subassembly disposed in the housing.

12. The electrical stimulation system of claim 11, wherein the connector assembly of the lead assembly is part of the control module.

13. The electrical stimulation system of claim 11, wherein the lead assembly comprises the lead and the electrical stimulation system further comprises a lead extension coupleable to the control module and the lead, wherein the connector assembly is part of the lead extension.

14. A method for stimulating patient tissue, the method comprising:
advancing a lead to a target stimulation location within a patient, the lead comprising a plurality of electrodes disposed along a distal portion of the lead, a plurality of terminals disposed along a proximal portion of the lead, and a plurality of conductors electrically coupling the plurality of terminals to the plurality of electrodes;
coupling the proximal portion of the lead to the connector assembly of claim 1; and
stimulating patient tissue using the plurality of electrodes.

15. The method of claim 14, wherein coupling the lead to the connector assembly comprises physically contacting at least one of the plurality of terminals to the contact region of the spring contact of at least one of the plurality of contact assemblies, the physical contact causing a bending deflection of the contact region of the spring contact while maintaining contact between the contact region and the lead.

16. A contact assembly, comprising:
a contact housing defining a lumen through the contact housing and a longitudinal axis along the lumen, wherein the contact housing is configured and arranged to receive a proximal portion of a lead or lead extension within the lumen of the contact housing, and
a spring contact disposed within the contact housing and having a contact region that extends diagonally with respect to longitudinal axis of the contact housing, wherein the contact region is positioned within the contact housing so that insertion of the proximal portion of the lead or lead extension into the contact housing results in a bending deflection of the contact region while maintaining contact between the contact region and the lead or lead extension.

17. A connector assembly, comprising
a plurality of the contact assemblies of claim 16 arranged in a transverse array with the lumens of the contact housings of the contact assemblies being spaced apart and parallel to each other.

18. A connector assembly, comprising
a plurality of the contact assemblies of claim 16 arranged in an axial array with the lumens of the contact housings of the contact assemblies being aligned to form a connector lumen.

19. A connector assembly, comprising:
a connector body having an elongated shape with a first end, an opposing second end, an inner circumferential wall, and a longitudinal axis, the connector body defining a port at the first end configured and arranged to receive a proximal portion of a lead or lead extension, the port opening to a cavity defined within the connector body and bound, in part, by the inner circumferential wall; and
a first contact assembly and a second contact assembly axially spaced-apart from one another within the cavity of the connector body and collectively forming a lumen that extends from the port along the longitudinal axis of the connector body, the first and second contact assemblies each comprising
a contact housing having a first sidewall, an opposing second sidewall, and an outer circumferential surface, the contact housing defining circumferential chamfers extending between the outer circumferential surface and each of the first and second sidewalls, and
a connector contact disposed in the contact housing and exposed to the lumen; and
a seal disposed within the cavity between the first contact assembly and the second contact assembly, the seal comprising
a deformable, washer-shaped seal body having an outer circumference, and
a deformable flange disposed around the outer circumference of the seal body;
wherein the seal is positioned between the contact housings of the first and second contact assemblies with the flange positioned between opposing ones of the circumferential chamfers of the contact housings of the first and second contact assemblies.

20. The connector assembly of claim 19, wherein the deformable seal body is axially compressed between the first and second connector assemblies, the axial compression causing the seal body to expand radially and the deformable flange to form a seal against the inner circumferential wall of the connector body and opposing ones of the circumferential chamfers of contact housings of the the first and second contact assemblies.

* * * * *